United States Patent [19]

Kramer et al.

[11] 4,000,976
[45] Jan. 4, 1977

[54] APPARATUS AND METHOD FOR PREPARING, DILUTING AND REPLICATING LABORATORY SAMPLES

[75] Inventors: Charles E. Kramer, Northbrook; Menachem Tiger, Mount Prospect, both of Ill.

[73] Assignee: G. D. Searle & Co., Skokie, Ill.

[22] Filed: Apr. 11, 1975

[21] Appl. No.: 567,349

Related U.S. Application Data

[63] Continuation of Ser. No. 312,894, Dec. 7, 1972, abandoned.

[52] U.S. Cl. .................................. 23/259; 141/98; 141/130
[51] Int. Cl.² ........................................ G01N 1/18
[58] Field of Search ............. 23/259, 253 R, 230 A; 141/83, 94, 98, 130

[56] References Cited

UNITED STATES PATENTS

| | | | |
|---|---|---|---|
| 3,193,358 | 7/1965 | Baruch | 23/253 R |
| 3,286,992 | 11/1966 | Armeniades et al. | 259/4 AB |
| 3,508,879 | 4/1970 | Findl et al. | 23/253 R |
| 3,525,591 | 8/1970 | Jungner et al. | 23/253 R |
| 3,536,449 | 10/1970 | Astle | 23/230 R |

*Primary Examiner*—Robert M. Reese
*Attorney, Agent, or Firm*—W. C. Ramm; P. J. Sgarbossa; H. A. Wegner

[57] ABSTRACT

Apparatus for diluting, replicating and establishing standards of chemical samples in sample trays, which samples are automatically prepared from specimen material in specimen trays. The apparatus processes a plurality of specimen trays, and prepares samples therefrom, depositing these samples in a plurality of sample trays. The specimen trays and the sample trays are automatically transported to a station where sample preparation, dilution, and replication is carried out according to predetermined instructions stored in the apparatus. The various trays may be uniquely coded for identification.

43 Claims, 12 Drawing Figures

APPARATUS AND METHOD FOR PREPARING, DILUTING AND REPLICATING LABORATORY SAMPLES

This is a continuation of application Ser. No. 312,894, filed Dec. 7, 1972, now abandoned.

This invention relates to an apparatus for the automatic preparation of samples from specimen materials. These samples may include portions of the original specimen material alone, dilutions of specimen material with a buffer material, and replications of any or all of the foregoing. Reagent material is selectively added to the samples to produce the samples in their final form. All of these manipulations of fluids are performed by the apparatus of this invention. Intermediate incubation of the samples may be desirable, and may be performed in the apparatus of this invention, though, the sample trays more probably will be transferred to incubation chambers in order to achieve greater throughput through the device of this invention.

BACKGROUND OF THE INVENTION

In the past, and especially in recent years, the laboratory techniques of competitive binding assay and competitive radioassay have become increasingly valuable tools for analysis of biological materials. These techniques have become particularly important in medical research for determining the presence or absence of particular biological substances which are indicative of particular medical conditions in a subject. While the term "radioimmunoassay" has frequently been used to describe all forms of competitive radioassay and competitive binding assay, many other forms of these more general terms besides radioimmunoassay are common laboratory procedures. Appropriate terms include radioenzymatic assay, radiostereoassay, saturation analysis, displacement analysis, and competitive protein binding.

Whatever the particular technique, the procedure usually involves the tedious preparation of a great multiplicity of samples from a smaller number of specimens. Dilution of the specimen material and replication of the samples produced is typical in these laboratory techniques. The samples must be handled a number of times to achieve dilution and replication as well as intermediate incubation and subsequent centrifugation. Because of the great number of discrete chemical mixtures involved, the processing of a single batch of specimens requires a considerable amount of time by laboratory personnel. Furthermore, because of the tedious nature of the manual steps involved, mistakes in the manual manipulations of specimens and samples are far too frequent. For these reasons, there has existed a chronic need for a device to process a batch of specimen materials and yield as a product samples ready for analysis along with sample standards and batch controls, with only a periodic requirement for manual attention.

At present, no appropriate device exists. The machines most useful in the preparation of samples for competitive binding assay have eliminated but a minor portion of the manual attention involved. For example, a laboratory device exists which will withdraw specimen material from a test tube in a first column of tubes, and deposit the specimen material in a mixture with a buffer diluent in an adjacent test tube in a second column of tubes. Processing of specimens can occur only on a one-to-one basis. That is, a single tube in the first, or specimen column can yield but a single sample in the second, or sample column. In competitive binding assay, however, it is frequently desirable to have a plurality of dilutions of each specimen and replicate samples of each dilution. Where two dilutions in duplicate are required from each specimen, four samples must be produced from each specimen processed. Where the specimen material, and two dilutions thereof are each required in triplicate, nine samples must be produced from each specimen. It can be seen that because of limitations imposed by the one-to-one production of samples from specimens with the above sample preparation unit, a single batch of specimen materials must be processed a plurality of times in order to produce the required number of samples. Also, the existing device has no provision for the creation of sample standards, or batch controls, which are essential in all forms of competitive binding assay. Furthermore, the specimen columns and the sample columns of test tubes are provided in the form of engagable test tube holders, which are engaged only during sample preparation and which must thereafter be disengaged so that the specimen tubes are again available for the preparation of additional samples in the recurring sample preparation steps which must be applied to each specimen. Also, the volume of reagent and buffer to be added must be manually adjusted. This adjustment must typically be made at the end of one cycle in the processing of a single specimen batch and before a subsequent cycle is initiated. The test tubes are thereby grouped in only a single column, usually from ten to fourteen in number, and the samples produced from a single specimen are not grouped together. This separation of samples from a common specimen, and the large number of test tube groupings involved, aggravate an existing problem of difficulty in sample identification.

SUMMARY OF THE INVENTION

It is a primary object of the present invention to automatically produce a plurality of samples from each of a number of specimens. For most applications, all of the samples produced from a single specimen are maintained in a group which is transported as a unit through the device of the present invention. This arrangement of proximity of the members of each sample group is maintained even though it may be necessary for the samples to be moved in and out of the unit of this invention, for purposes such as incubation. The proximity of all samples from a single specimen is maintainable even after processing in the present apparatus is completed. This is particularly desirable where the samples are to be subjected to further treatment or analysis, such as centrifugation or measurement of radioactivity.

It is a further object of this invention to obviate problems of sample identification. This is achieved through the use of a sample tray having a rectangular array of sample receptacles. With such a rectangular array, an orderly pattern of samples produced from specimens may be repeated from sample tray to sample tray. That is, particular receptacle rows within the sample trays may be used exclusively for receiving specimen material in an undiluted form, e.g., every third row. Each succeeding row could be dedicated to first and second dilutions respectively of the preceding undiluted specimen material. By the same token, receptacle columns within the sample tray may be used in a dedicated fashion. For example, the second and third columns in a tray might be used exclusively for replicates of adjacent samples located in the first column.

A further object of the invention is to produce all of the necessary samples from a single specimen at one time, and thereby eliminate the necessity for recycling the specimens through the apparatus of this invention. While it may be desirable to recycle the sample trays through the invention either to add reagent after a time lapse or for some other purpose, all of the specimen-buffer mixtures, hereinafter referred to as "samples", are originally established during a single processing cycle of the individual specimens. In this context, as with the foregoing considerations, it can be seen that the use of a fixed rectangular array of sample receptacles solves a number of distinct problems which have been associated with sample preparation in the past. As previously noted, this rectangular array of sample receptacles is treated as a unit throughout the entire operation of the apparatus of this invention, and frequently during subsequent processing.

Furthermore, the rectangular array of sample receptacles solves additional problems of sample preparation in particular applications. For example, it has heretofore been impossible to add different reagents to each sample in a set of replicate samples during a single sample processing cycle in a sample preparation unit. With the present invention, however, tips for despensing different reagents may be located above the different columns in the rectangular sample receptacle array at a reagent dosing position. Different reagents can thereby be added to the separate replicates of a particular specimen or specimen dilution in the sample receptacles. Samples are thereby concurrently modified for subsequent testing for several separate reactions with different reagents.

It is a further object of a preferred embodiment of the invention to provide automated identification of each specimen and each sample. As previously noted, the sample receptacles within a tray may be dedicated in a particular predetermined pattern, as determined by instructions initially given to the process controller of the invention. Thus, the processing characteristics of a sample receptacle can be classified according to its position in a sample tray. Preferably, a tray identification means is provided with this invention. A tray identification device is physically connected to each tray to impart a unique identifiable feature to the tray. This unique identifiable feature is automatically determinable, by means of a code reading device connected to the process controller. From the various pieces of information transmitted to the process controller, the unique characteristics of each sample may be ascertained, and correlation of samples with specimens is a simple matter. Another object of the invention is to provide automatically for the preparation of the sample standards and batch controls that are necessary for subsequent analysis of the unknown samples produced from the specimen materials. Standards are produced automatically from instructions to the process controller and trays containing the standard samples are identifiable by appropriate coding of the tray identifying device associated therewith.

Another object of a preferred embodiment of the invention is to utilize a single movable tip for both aspiration and dispensation of fluids without the requirement for flushing the tip with a rinsing liquid prior to the preparation of each sample. This requirement exists in all present devices which utilize a single tip for aspirating specimen material and dispensing sample material, but is avoided with the present invention through the use of a unique fluid circuit construction. This construction creates a scouring action of the walls plus turbulence within the fluid profile adjacent to the movable tip, and thereby removes lingering particles of fluid and renders unnecessary a subsequent rinsing operation without sacrificing the reliability of results from subsequent sample measurements.

In a broad aspect this invention is a sample preparation apparatus for diluting, replicating and establishing standards of chemical samples for subsequent analysis comprising: a tray transport unit having a conveyor means for transporting separate specimen trays having an array of receptacles and containing discrete chemical specimens, and for transporting separate sample trays having an array of receptacles for containing discrete chemical samples; a buffer material reservoir; a dosing station having a dosing means in gated communication with said buffer material reservoir for aspirating material from receptacles in said specimen trays and for dispensing material to a plurality of other receptacles from a single receptacle in a specimen tray; a reagent reservoir means; a reagent addition means for adding reagent material to receptacles in said trays; and a process controller for automatically governing fluid flow in said dosing station and in said reagent addition means according to predetermined instructions.

DETAILED DESCRIPTION OF THE INVENTION

This invention may be further illustrated by reference to the accompanying drawings in which.

Figure 1:
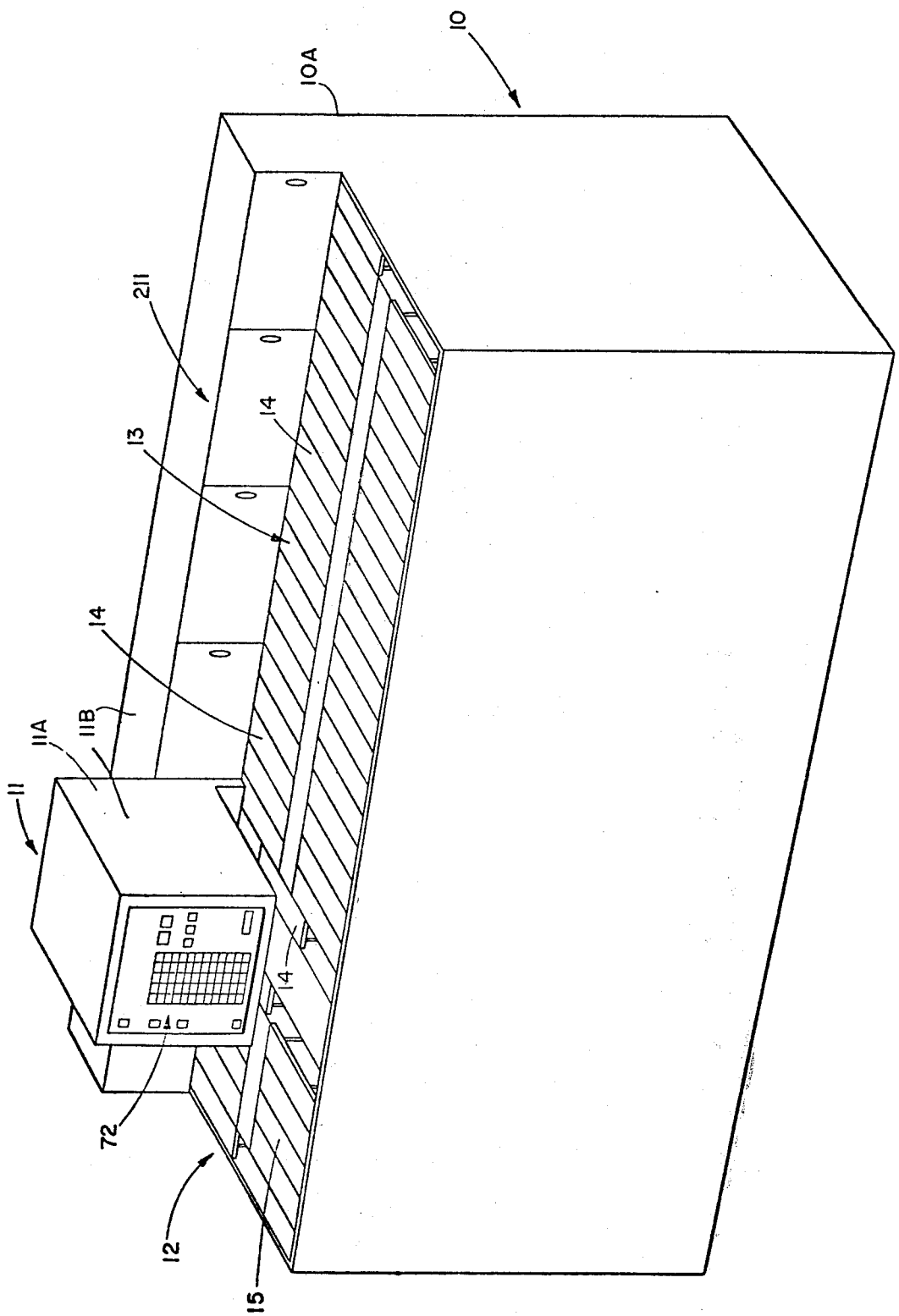
FIG. 1 is a perspective view of a cabinet containing the apparatus of this invention.
Figure 2A:
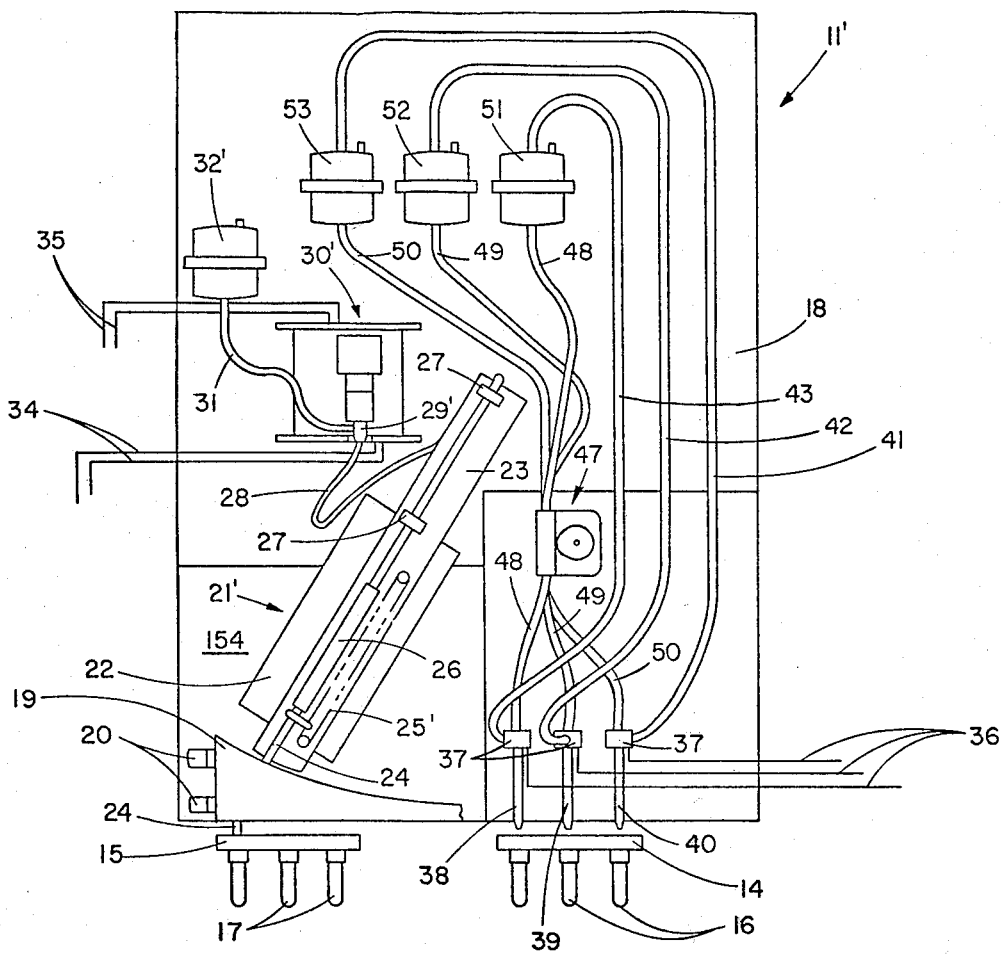
FIG. 2A is an alternative embodiment of the dosing station.
Figure 2A:
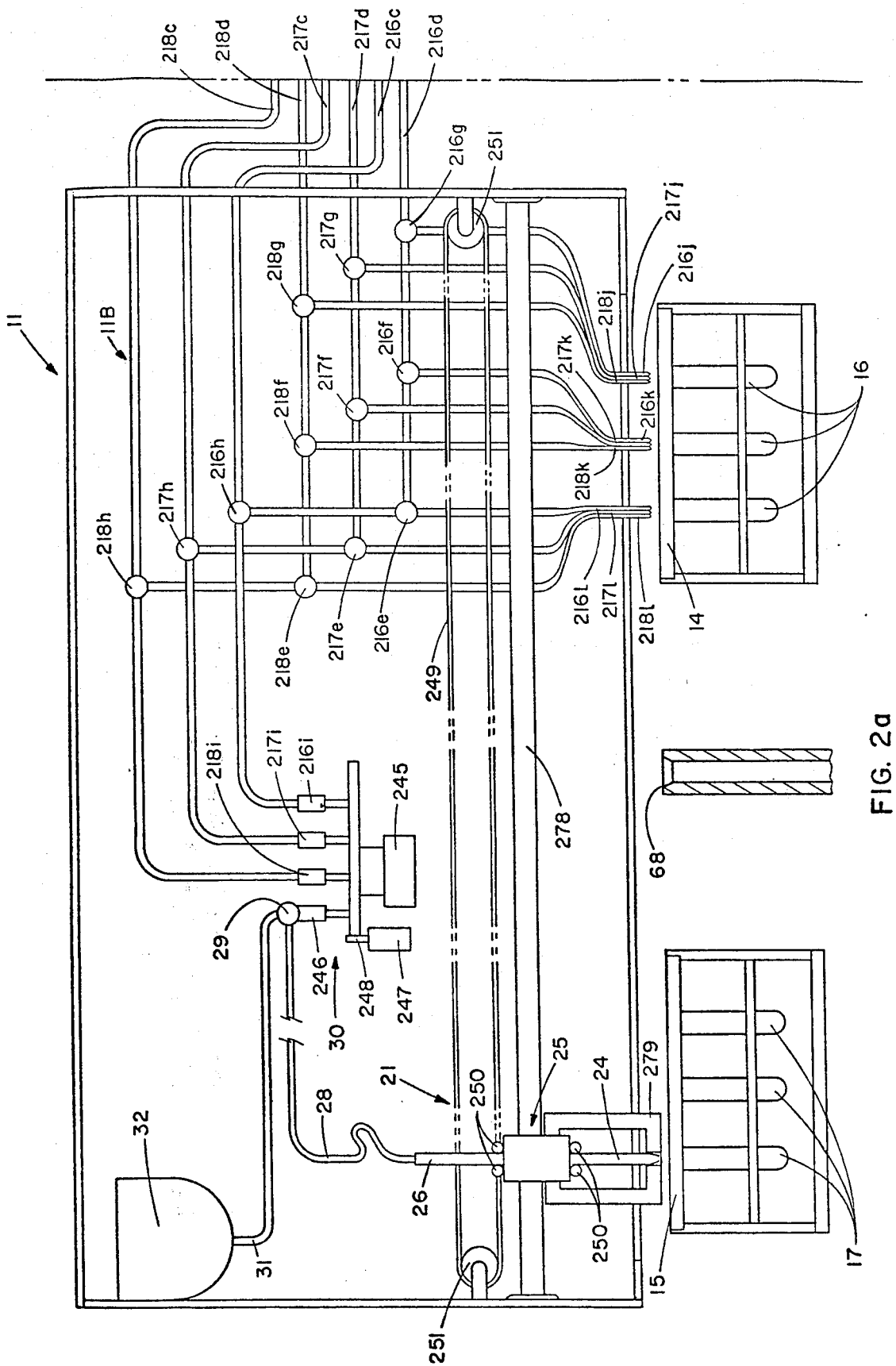
Figure 2B:
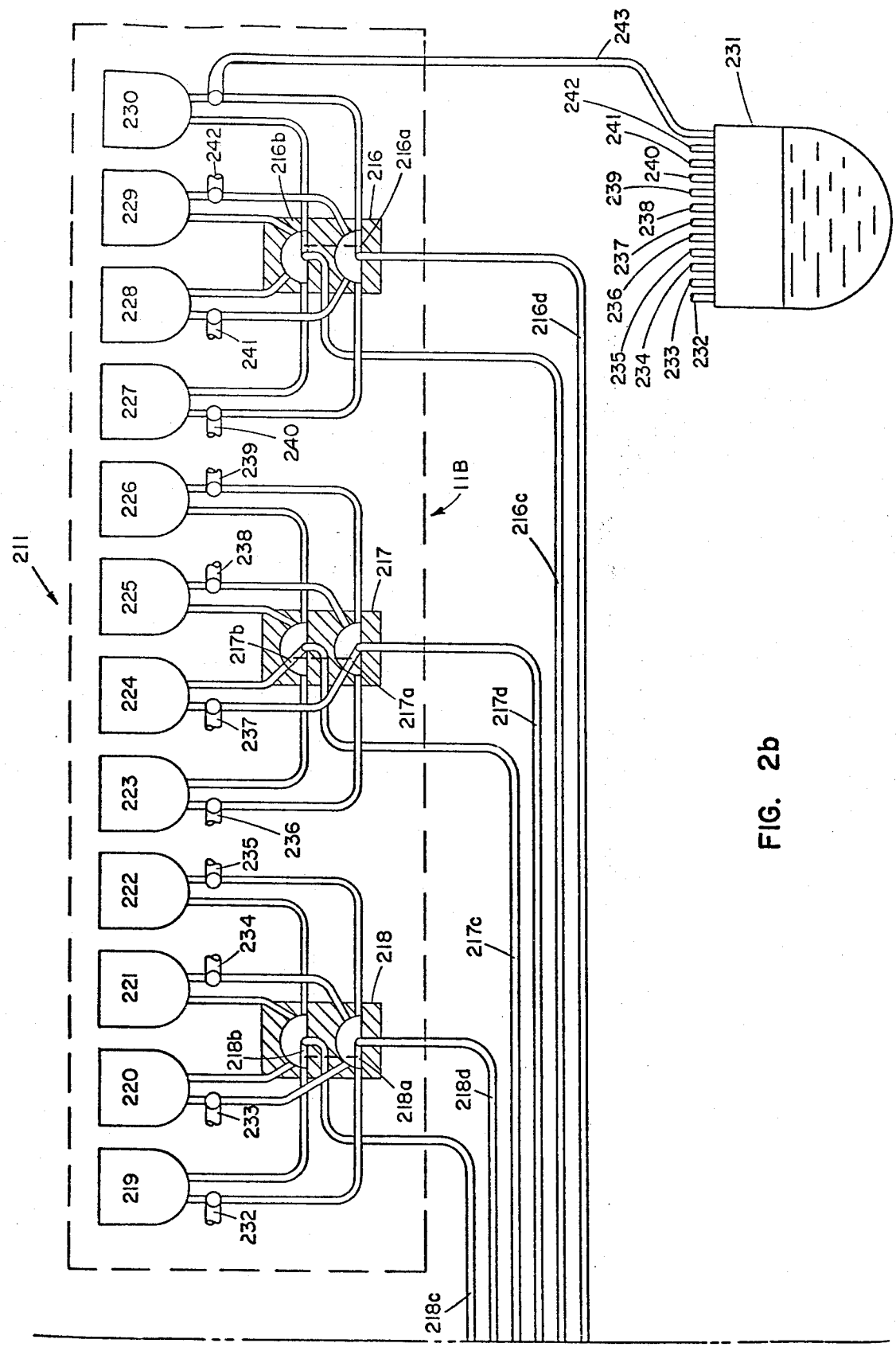
FIG. 2 is an elevational schematic view of the dosing station and back section of this invention.

Referring now to FIGS. 1 and 2, there is illustrated a sample preparation unit 10 capable of diluting specimens contained in specimen receptacles 17 in specimen trays 15 and of passing these diluted specimens as samples to sample receptacles 16 in sample trays 14, either as single, duplicate, or triplicate samples. Sample preparation unit 10 is also capable of automatically establishing standards of chemical samples in receptacles 16 in the sample trays 14. The unknown samples and the sample standards are produced in the sample receptacles 16 in sample trays 14 by the unit 10 for subsequent analysis.

Figure 5:
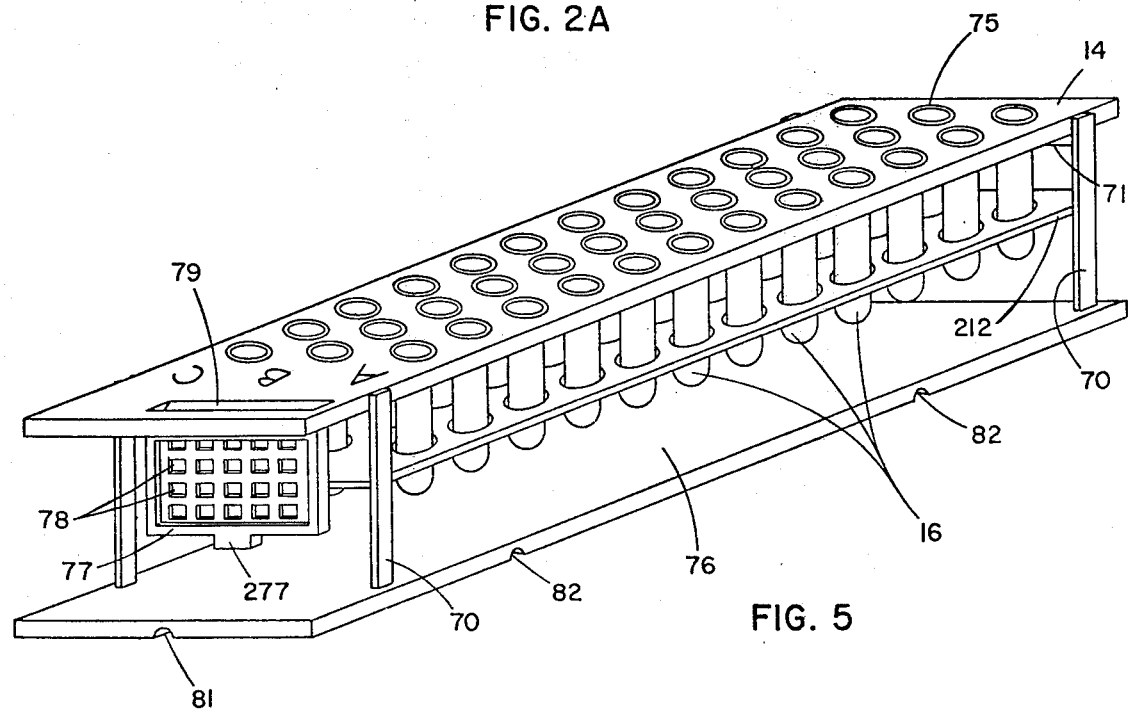
FIG. 5 is a perspective view of a tray and tray support used in the cabinet of FIG. 1.
Figure 9:
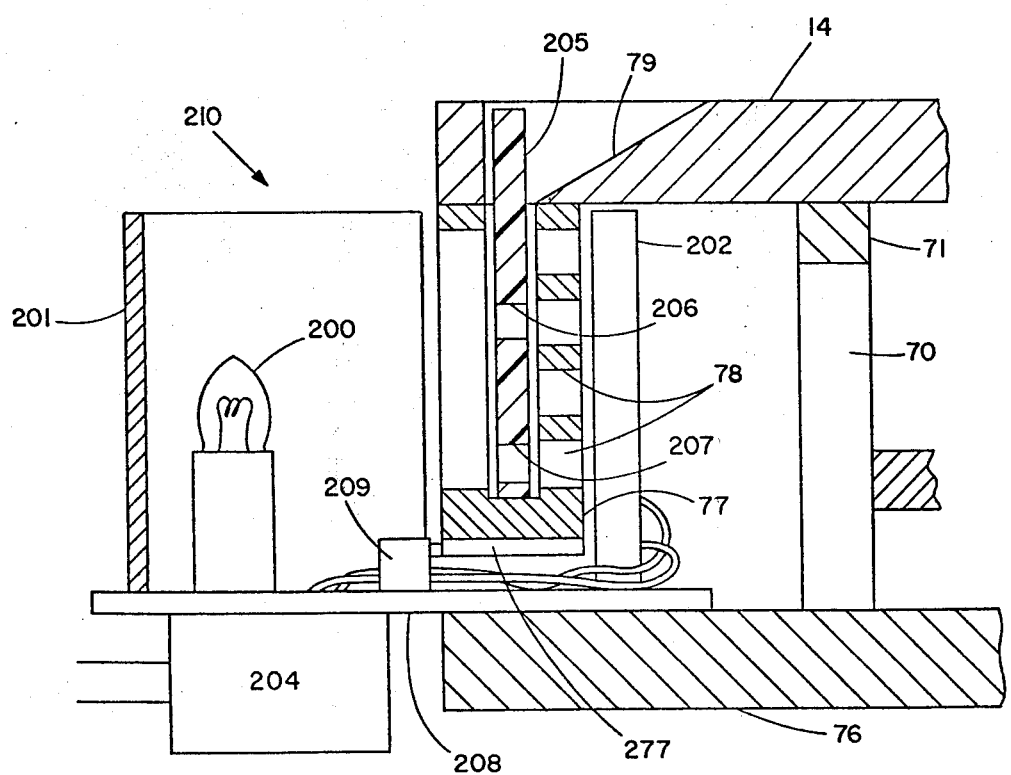
FIG. 9 is an isolated view of a code reading device used in this invention.
Figure 10:
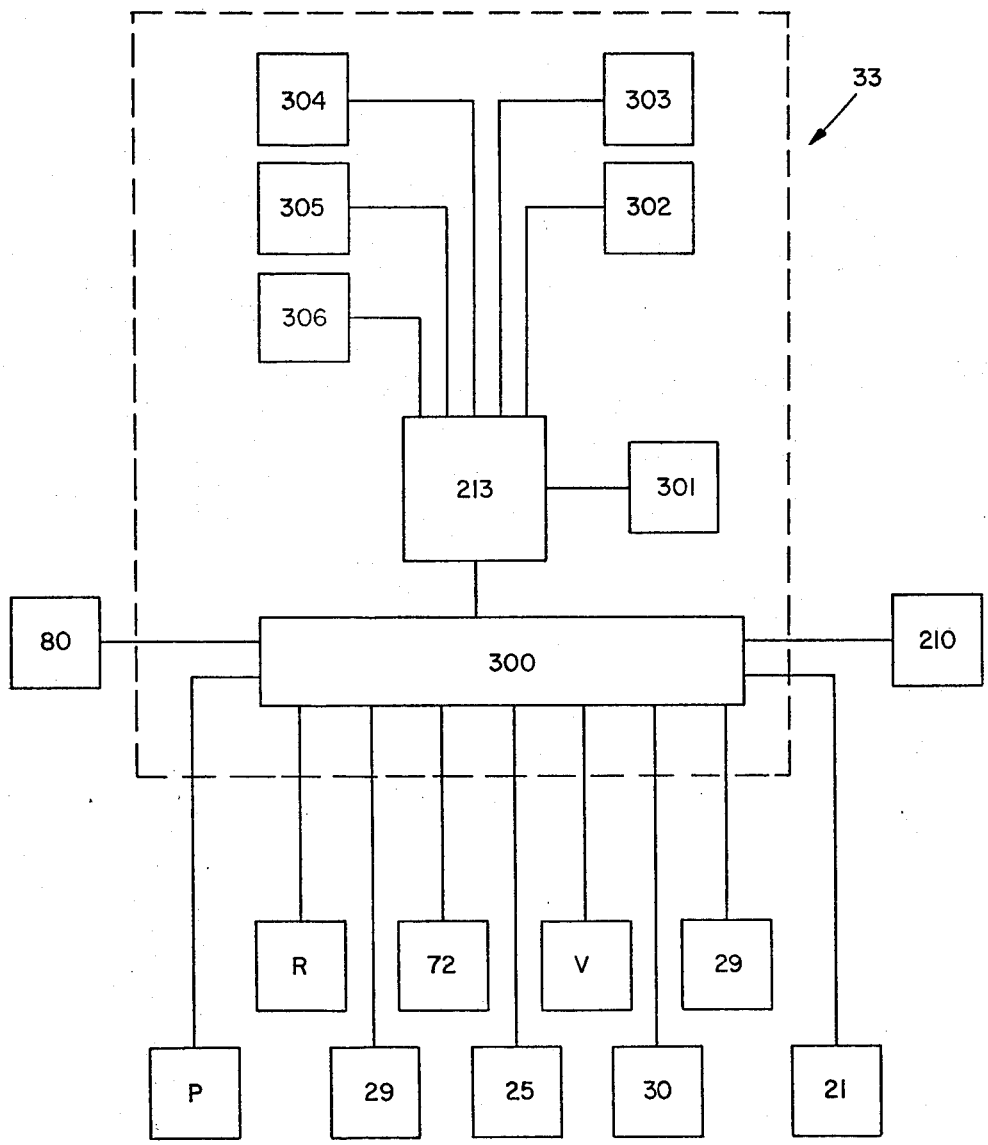
FIG. 10 is a block diagram of connections to the central processor of this invention.

The sample preparation unit 10 is comprised of a back section 211, a specimen section 12 containing separate specimen trays 15, a sample section 13 containing separate sample trays 14, and a dosing station 11 extending over adjacent portions of sections 12 and 13. The foregoing elements are all supported upon a base support assembly 10A of unit 10. The specimen trays 15 each contain a rectangular array of specimen receptacles 17 in the form of test tubes positioned in three columns and twelve rows. Similarly, each of the sample trays 14 has a rectangular array of sample receptacles 16, in the form of test tubes, positioned in three columns and twelve rows. Each of the sample tubes 16 is designed to accomodate a discrete chemical sample. The sample tubes 16 and the specimen tubes 17 are of identical construction, and differ from each other only by the type of substance contained therein. Similarly, sample trays 14 and specimen trays 15 are of identical construction, and differ from each other only by the type of material each accomodates. The sample trays 14 are positioned together with tray support blocks 76 as illustrated in FIG. 5. The tray support blocks 76 have corner supports 70 arising therefrom, with crossbars 71 joining the vertical supports 70 and with a perforated tube stabilizing sheet 212 confined between vertical supports 70. The tray 14 is merely placed on the tray supporting structure and rests on the crossbars 71. The samples 16 are restrained by the stabilizing sheet 212 and by the sample 75 inserts 75. The sample trays are further described in the pending U.S. patent application of Rolf Meyer and John E. Burgess, No. 483,024, filed June 25, 1974, now abandoned; as a continuation-in-part of Ser. No. 292,738, filed on Sept. 27, 1972, now abandoned. Each tray 14 is provided with a tray identification means which includes a removable device, such as a plastic or cardboard card, coded with a unique identifying code. The card may comprise a matrix of removable sections, typically discontinuously joined to the card for ease of removal. The card can be coded by merely removing selected ones of these removable sections. The card is then physically associated with a tray by insertion into a slot 79 in the upper surface of a tray 14. Slot 79 leads to an encasing structure 77 depending from the underside of tray 14. The depending structure 77 has a matrix of apertures 78 on its expansive surface closest to the tray receptacles. The sample preparation apparatus 10 is provided with a code reading means 210 as shown in FIG. 9 for reading the codes of the tray identifying devices. A separate code reading means is provided for the specimen trays 15 and for the sample trays 14. These code reading means 210 are each mounted on a platform 208 which is moved perpendicular to the plane of FIG. 9 in front of the supports 70 to read the code on a card 205 positioned as indicated prior to processing each tray. Position sensing switches 209 sense the location of the tabs 277 at the bottom of the encasing structure 77 and thus properly position the card readers 210 with respect to the encasing structure 77. Each of the code readers 210 utilizes a light emission means 200 located within a light shield 201 for projecting light into the apertures 78 in the encasing structure 77. Where sections have been removed from the card 205, as at 206 and 207, the light will pass through card 205 and through the apertures 78 of structure 77, and will strike the optical reader 202, which is of conventional design and is connected by electrical wires to a read-out unit 204. Where sections have not been removed from the card 205, however, light will be blocked and prevented from striking the optical reader 202. Read-out unit 204 translates the output of the reader 202 into a number in machine readable form, and transmits that number from the code reading device 210 to the process controller 33 as indicated in FIG. 10. In this manner, the portable tray identifying card can be used to impart a unique identifiable feature to each tray. In addition, the code reader 210 supplies information as to whether or not the specimens in the specimen trays are to be used to generate standard samples. As previously discussed, this system for tray identification, when combined with the plan of sample receptacle identification through dedication of particular sample receptacle positions to predetermined modifications of a specimen located at a particular specimen receptacle position, can be used to uniquely identify the content of each and every sample receptacle 16.

Figure 7:
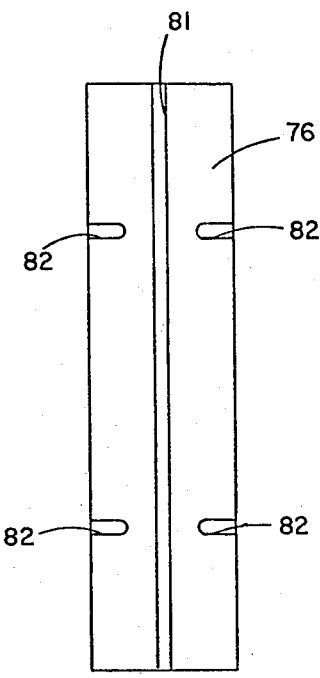
FIG. 7 is an enlarged bottom view of a tray support of FIGS. 5 and 6.
Figure 6:
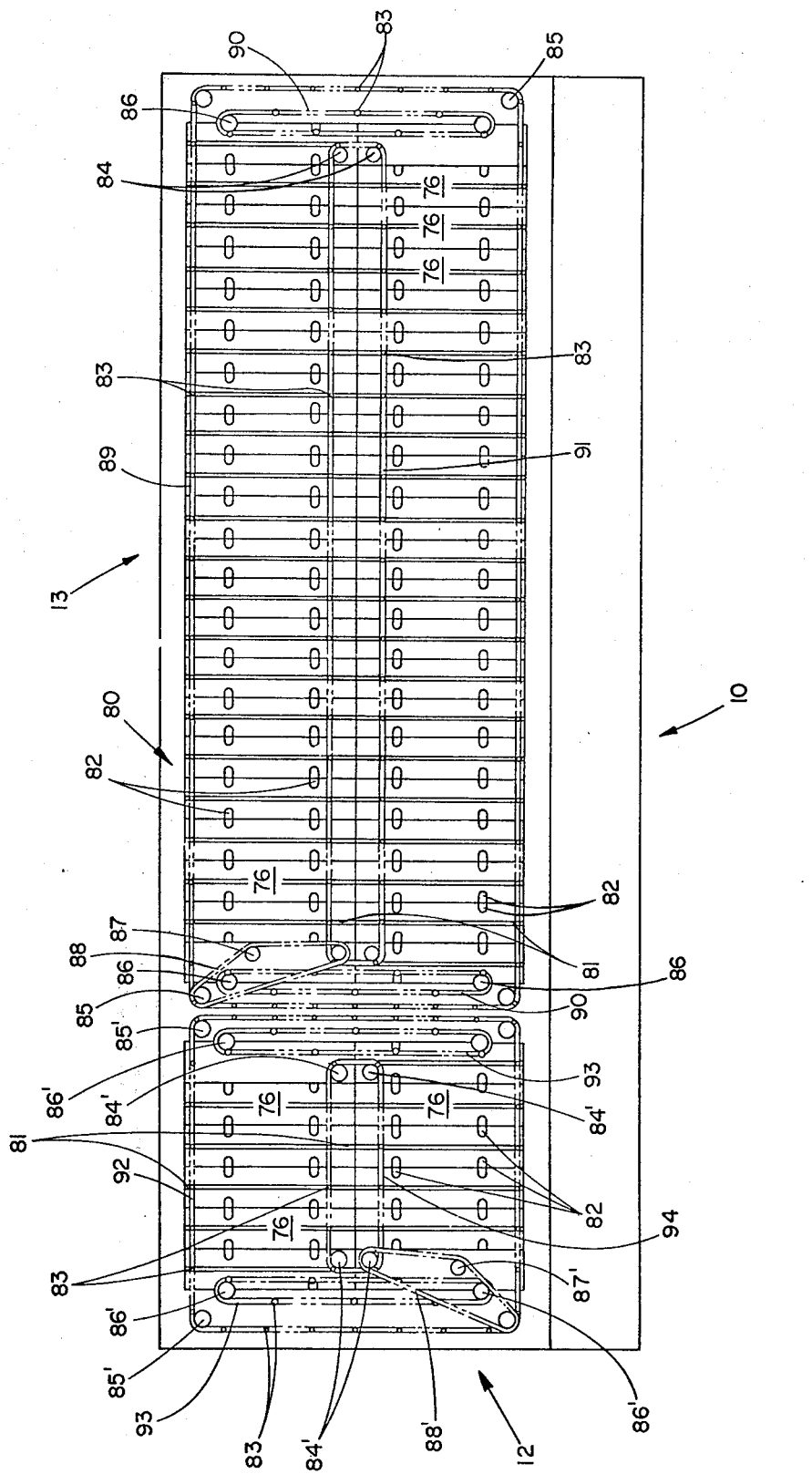
FIG. 6 is a plan view looking up from the bottom of FIG. 1.

As illustrated in FIGS. 5, 6, and 7, each of the tray support blocks 76 has lateral grooves 82 and a longitudinal groove 81 in its undersurface. These grooves 81 and 82 accommodate pins 83 projecting upward from the various chains of the conveyor system 80 so that the tray support blocks 76 may be moved either about the sample section 13 or specimen section 12 by the projecting pins 83. Thus both specimen trays and sample trays are moved by conveyor system 80 in independent spaced but adjacent paths. For example, in FIG. 1 it may be seen that in sample section 13, the sample trays are arranged in extended, side by side lines along the back and front of unit 10, so that the trays move laterally in these lines in the direction of the tray receptacle rows. By contrast, at the ends of these lines, at the right hand side of the machine and under dosing station 11, the tray movement is longitudinal, in the direction of the tray receptacle columns. In this manner a closed loop sample tray path is defined, and the specimen section 12 also defines an independent closed loop path. Although in the present embodiment these sample tray and specimen tray paths are shown as closed loop paths, they may also be discontinuous; however, both paths should have portions proximate to dosing station 11, and all trays should be maintained in a horizontal upright attitude throughout the paths.

Conveyor system 80, and the manner in which the trays are conveyed in the respective paths, will now be discussed in more detail. Beneath the sample section 13 there exists a peripheral chain 89, and interior chain 91, and tray feeding chains 90. The peripheral chain 89 and the interior chain 91 cooperate to carry the tray support blocks 76, and hence the trays 14, in a direction perpendicular to the sample receptacle columns. Chain 89 is driven about the peripheral sprockets 85 positioned directly beneath the sample section 13. Similarly, interior chain 91 is carried about the sprockets 84 located beneath sample section 13 and is driven from one of the peripheral sprockets 85 by means of a connecting chain 88 which also passes about an idler tension maintaining sprocket 87. The chains 89 and 91 are driven counter-clockwise in FIG. 6 so that the upper line of tray support blocks 76 is carried toward the dosing station (and toward the specimen section) by the pins 83 projecting upward into the slots 81 from chains 89 and 91. Through the same mechanism, the tray support blocks 76 in the lower line are carried away from the dosing station and the specimen section by means of the pins 83 projecting into the slots 81.

After the termination of processing a sample tray 14, the tray support blocks 76 will be in the position indicated in FIG. 6, with vacant locations at the extreme upper left and at the extreme lower right in FIG. 6 beneath the sample section 13. The process controller actuates one of the driving sprockets 85 to drive the chains 89 and 91 so that each of the tray support blocks 76 advances counter-clockwise one tray position. This means that a tray support block 76 will then occupy each of the tray support positions shown blank in FIG. 6. Thereupon, the pins 83 projecting upward from the feed chains 90 will be received in the adjacent slots 82 of the tray support blocks 76 which have moved into the previously vacant positions. Feed chains 90 periodically advance clockwise about the feed chain sprockets 86, upon actuation by the process controller, to move the sample trays 14 in the direction of the receptacle columns past the dosing station. As viewed from the perspective of the operator of the unit (see FIG. 1), the sample trays move in a clockwise direction over the sample tray path. Samples are deposited in the sample receptacles at the dosing stations until the tray support blocks 76 are once again in the positions illustrated in FIG. 6, whereupon counter-clockwise advancement of the tray support blocks 76 is repeated.

In a similar fashion, the peripheral chain 92 and the interior chain 94 below the specimen section 12 advance in a clockwise direction about the peripheral sprockets 85' and interior sprockets 84' respectively, located below the specimen section 12. As before, the advancement of the interior chain 94 is by means of a connecting chain 88' passing over an idler sprocket 87' and driven by one of the peripheral sprockets 85'. When one of the specimen trays 15 has been completely processed, the tray support blocks 76 beneath the specimen section 12 will be at the positions indicated in FIG. 6. The pins 83 in the peripheral chain 92 and interior chain 94 are received in the longitudinal slots 81. Clockwise advancement of chains 92 and 94 advance the tray support blocks 76 one position in a clockwise direction. Pins 83 projecting upward from the specimen feed chains 93 are received in the adjacent lateral slots 82 of the tray support blocks 76 moving into the previously vacant positions. Upon actuation by the process controller, the specimen feed chains 93 periodically advance in a counter-clockwise direction about sprockets 86', thus moving a specimen tray in the direction of its receptacle columns past the dosing station. As viewed from the perspective of the operator of the unit, the specimen trays move in a counter-clockwise direction over the specimen tray path.

As will be apparent from the above, the adjacent portions of the specimen tray path and the sample tray path are those above sample feed chain 90 and specimen feed chain 73. dosing station 11 is positioned above these adjacent path portions as may be seen by comparing FIGS. 6 and 1, and the adjacent path portions under station 11 run parallel to each other.

Since a plurality of sample receptacles typically receive sample material from a single specimen receptacle, it can be seen that the portion of the conveyor means 80 located beneath the sample section 13 advances at a greater pace than does the portion of the conveyor system located beneath the specimen section 12. To accommodate a greater number of sample trays 14 as compared to the number of specimen trays 15, the sample section 13 is constructed much larger than the specimen section 12.

Referring now to FIG. 2, the dosing station 11 of FIG. 1 is schematically illustrated in an isolated view with its cover and control panel containing instruction buttons 72 removed. The instruction buttons 72 serve to provide the process controller 33, which may be comprised of a conventional special purpose computer 213 in FIG. 10, such as the Nuclear-Chicago Corporation Computer Model PDS-3, pre-programmed with predetermined instructions to govern fluid flow and tray advancement in the sample processing unit 10. The central processor 33 is either located beneath the conveyor system 80, in the back section 211, or possibly in a completely different cabinet. Its particular location makes no difference as long as the electrical connections for automatically controlling fluid flow and tray advancement exist as schematically illustrated in FIG. 10.

Dosing station 11 includes a processing or dosing means 11A by which buffer and specimen from trays 15 are processed in making up samples for analysis.

The dosing means 11A of the embodiment of the invention illustrated includes a dosing pump mechanism 30 for aspirating and dispensing material, a single movable dosing tip 24 included in a tip carriage assembly 25, for movement of the dosing tip in the vertical direction tip transport means 21, for movement of the tip carriage in the lateral direction, as well as a valve 29 in series between pump mechanism 30 and a buffer reservoir 32, which is housed within dosing station 11. The dosing pump mechanism 30 will typically include a conventional dosing pump 246 such as disclosed in U.S. Pat. 3,615,240, operated by a linear actuator 245, such as disclosed in U.S. Pat. No. 3,576,454. The dosing pump mechanism 30 is electrically connected to the central processor 33 and the movement of the linear actuator 245 is governed by the central processor 33 through a conventional interface, such as an optical reader 247 which senses the movement of a Moire Scale 248 connected to the movable element of the linear actuator the foregoing pump, actuator and central processor enable continuous and precise control of the volumes of fluid aspirated and dispensed by dosing means 11A, including a continuously variable aspiration volume, as well as dispensation of such volume accurately in proportional fractions. Valve 29 is also connected to and controlled by central processor 33 to allow or prevent flow of buffer material from buffer reservoir 32 to dosing tip assembly 21. Although only one buffer reservoir 32 is shown in the embodiment in FIG. 2, an alternate configuration would add three more buffer reservoirs with a four position valve (similar to half of reagent switching valve 218) connecting each of the reservoirs in turn to valve 29. This configuration would expedite a rapid changeover from one buffer material to another.

Together, valve 29 and the dosing pump mechanism 30 serve as a dilution control means operating under the control of process controller 33. The dilution control means has an actuation system for controlling the dosing means of dosing station 11 to distribute a plurality of predetermined dilutions of a single specimen material, originally contained in a single specimen receptacle 17 in a specimen tray, into a plurality of sample receptacles 16. A buffer material resevoir 32 provides a diluent, or buffer liquid through a connecting tube 31 to the valve 29 and dosing pump 30, from where it is passed to the dosing tip 24 when the valve position or valve 29 allows flow from pump 246 to line 28.

Tip transport assembly 21 includes chain 249 with its associated sprockets 251 retaining the chain at each end, as well as a guide rod 278. Both sprockets 251 and each end of rod 278 are secured to opposite walls of the housing of dosing station 11, with the sprockets just above the ends of rod 278. In this way the chain and rod extend laterally and parallel to each other over adjacent portions of both specimen and sample tray paths. More specifically (see FIG. 2a) the chain 249 with rod 278 extends across the entire width of adjacent specimen and sample trays when the trays are under dosing station 11, transverse to the direction of movement of the trays, but parallel to the receptacle rows of the trays. In this way tip transport means 21 defines a dosing position for the entire buffer and specimen processing means 11A, and the sample and specimen trays beneath the dosing station 11. Thus, conveyor system 80 is controlled by process controller 33 to bring successive rows of specimen and sample trays which are to be processed to the dosing position by conveying the trays to a position such that the tray rows to be processed are aligned with the members of tip transport assembly 21.

Tip carriage assembly 25 rides upon guide rod 278 and is also attached to chain 249 near its upper end so that in order to move the assembly, the chain is advanced in one direction or the other. Tip 24 is movably mounted within assembly 25 and rides vertically up and down on upper end and lower roller pairs 250 in response to a reversible motor controlled by process controller 33. In this manner, tip 24 is made to access receptacles aligned below transport assembly 21 at the dosing position, both on specimen trays and on sample trays, depending on the procedure being implemented.

The motion and operation of the dosing tip 24 produced by the tip transport assembly 21 and tip carriage assembly 25 may be described as follows: to aspirate specimen material, a motor within the tip carriage assembly 25 drives the movable tip 24 vertically downward into one of the specimen receptacles 17. Valve 29 is actuated by the process controller 33 to allow specimen material to be aspirated into the tip 24 by means of the suction produced in the dosing pump 246. The motor within the tip carriage 25 is reversed to withdraw the dosing tip 24 up through the rollers 250 to the position indicated in FIG. 2. As the tip 24 is withdrawn, the tip wiping means 279 wipes off any fluid which has adhered to the outside of the tip.

To dispense material into the sample receptacles 16, the chain 249 is advanced counter-clockwise, thereby carrying the tip 24 to the right along the guide rod 278. When tip 24 has moved to the right in FIG. 2 and is positioned vertically above one of the sample receptacles 16, the valve 29 is positioned so as to connect the dosing pump 246 with the dosing tip 24. As directed by the process controller 33, the actuator 245 drives the dosing pump 246 so as to deposit a precise quantity of the specimen into one of the sample receptacles 16. If duplicate or triplicate samples are desired, the tip 24 is positioned above the other sample receptacle 16 and additional quantities of the specimen is dispensed. When dosing of sample material into the sample receptacles 16 has been concluded for a particular specimen, chain 249 reverses direction and advances in a clockwise direction, carrying tip carriage assembly 25 to the left in FIG. 2 for subsequent operations. If a dilution of the original specimen is desired, the tip 24 is positioned over one of the other specimen receptacles 17 and valve 29 is positioned so as to connect the dosing pump 246 to the buffer reservoir 32. Sufficient buffer is drawn into the pump to perform the desired dilution. After valve 29 is repositioned so as to connect the pump 246 and the tip 24, the remaining aspirated specimen material plus the additional buffer is dispensed into the specimen receptacle 17. This diluted specimen can be aspirated for replicating and performing further dilutions, if required. After each of the sample tubes 16 in a row has been dosed with sample material, the tray 15 advances one row position so that the sample receptacles 16 that have just been dosed with sample material are moved to reagent dosing positions.

Dosing station 11 not only includes dosing means 11A, but it also includes most of a reagent addition means 11B, with the remainder thereof being located in back section 211, as indicated in FIGS. 2a and b. The reagent addition means of FIG. 2 is comprised of several reagent pumps 216i, 217i, and outlet means in the form of, and a plurality of reagent dispensing tips located above the reagent dosing position for each receptacle column several reagent reservoir switching valves 216, 217 and 218, as well as several pump control valves and dispensing valves. All of these members are mounted within dosing station 11, except for valves 216, 217 and 218, which are mounted within back section 211, as illustrated.

In the embodiment illustrated in FIGS. 2a and b, the tips are arranged in three groups of three tips each, tip 216j, 217j and 218j comprising one group, tips 216k, 217k and 218k comprising a second group, and tips 216l, 217l and 218l comprising a third group. The tips of each group are in parallel abutting relationship, with this close physical association enabling the three tips of the group to dispense into the same receptacle. The three tip groups are supported side by side within dosing station 11 over the sample tray path, in alignment with the columns of the tray, as well as being spaced the equivalent of one tray row downstream of dosing means 11A and its dosing position. The tip groups thus define an overall reagent addition position for reagent dispensing means 11B and the sample trays, located immediately back of the dosing position on the sample tray path. Accordingly, when conveyor system 80 brings a row of a sample tray to the dosing position to cooperate with dosing means 11A, the immediately preceding row of that tray which was just processed is automatically positioned at the reagent addition position, with each receptacle of that row under a tip group, for the dispensing of appropriate reagents.

The reagent addition position may be thought of as comprising a right hand reagent dosing position over the right hand sample tray column, a center reagent dosing position over the center sample tray column, and a left hand reagent dosing position over the left hand sample column. Tips 216j, 217j, and 218j are located above the right hand reagent dosing position, while tips 216l, 217l, and 218l are located above the left hand reagent dosing position. Tips 216k, 217k, and 218k are located above the center reagent dosing position. A plurality of separate reagent reservoirs 219–230 are divided into three groups of four reservoirs each containing different ones or at least four different reagents, and all are supported within back section 211. They are connected to the reagent dispensing tips above each reagent dosing position in alternative communication with that dosing position. That is, one of reagent reservoirs 219 through 222 are connected by reagent reservoir switching valve 218 to lines 218c and d, and dispensing valves 218e, f and g, and thereby to reagent dosing tips 218j, 218k, and 218l. Reagent reservoirs 223 through 226 are similarly connected to reagent dosing tips 217j, 217k, and 217l, while reagent reservoirs 227 through 230 are similarly connected to reagent dosing tips 216j, 216k, and 216l. In addition, for dispensing a reagent from any one of reservoirs 219 through 222 into any of the sample receptacles, pump control valve 218h as well as dispensing valves 218e, 218f, or 218g must be positioned so as to connect pump 218i to tip 218j, 218k, or 218l, and similarly for the remaining reagent reservoirs and their associated tips.

As will be noted from FIGS. 2a and b, the lines 218c and d define a closed fluid circuit, with reagent switching valve 218, dispensing valves 218e, f and g, and pump control valve 218h in series in this circuit. Each dispensing valve also connects respectively to one of the tips 218l, 218k and 218j, which are closed off until reagent is to be dispensed, while pump control valve 218h is also connected to pump 218i, and controls the application and disconnection of the pump to the closed fluid circuit. The same arrangement is twice more repeated for the remaining two groups of reagent reservoirs. The closed fluid circuit for each group of reagent reservoirs enables the pump to circulate the reagent in the circuits so as to be in readiness for immediate dispensation on demand. Thus, when reagent is not being dispensed into any of the sample receptacles, valves 218e, 218f, and 218g are positioned so that reagent not dispensed is passed back to the reagent switchings valve 218, which contains valve elements 218a and 218b which move together. In this manner, reagent from any one of the reagent reservoirs 219, 220, 221, or 222 may be dispensed into sample receptacles at the reagent dosing position. With the valve elements 218a and 218b in the positions indicated, a circular path of reagent flow is formed from the reagent reservoir 219, through valve element 218b and through line 218c. Valve 218h initially allows reagent from line 218c to enter the dosing pump 218i when dosing pump 218i is in a position to take up reagent. The valve 218h is then switched to allow reagent to flow from the reagent dosing pump 218i through line 218d, valve element 218a, and back to reservoir 219. Whenever the valve elements 218a and 218b are moved to draw reagent from a different reservoir, the process controller 33 will operate the pump actuator 245 and valves 218e, 218f, 218g, and 218h plus the appropriate valve to waste outlets 232, 233, 234, or 235 in a preprogrammed cycle to purge the lines, valves, tips, and pump of the previous reagent. Reagent pumped during this purge cycle would be pumped into the waste reservoir 231 for disposal. If valves 218e, 218f, and 218g are opened by process controller 33 during the expulsion stroke of the dosing pump 218i, reagent will be dispensed into the sample receptacles located at the reagent dosing position. Otherwise, the pump 218i will merely circulate the reagent. The component elements comparable to those discussed in connection with reservoir 219, as indicated by suffix designation, associated with the reservoirs 223 through 226 will similarly allow fluid to flow from a selected one of these reservoirs into sample receptacles at the reagent dosing positions. In the same manner, through comparable component elements, reagent from the reservoirs 227 through 230 may be passed to the sample receptacles at the reagent dosing positions. In all instances, waste outlets 232 through 243 are provided to the waste receptacle 231. All of the valves and valve elements in the reagent addition means depicted are governed by the process controller and are collectively represented by the designation V in FIG. 10.

It can be seen that the reagent reservoirs 219 through 230, located in the back section 211 of the sample preparation unit, permit reagent to be dispensed to sample receptacles using a multi-channel, multi-purpose fluid system. In this manner, if the reagent reservoirs 219 through 222, 223 through 226, and 227 through 230 are provided with four different reagents in a repeated pattern, different reagents may be added to the sample receptacles at the different reagent dosing positions over each receptacle column or a tray, or alternatively the same reagent or combination of reagents may be added to all of the sample receptacles. This, of course, would be determined by instructions to the process controller.

An alternate embodiment of the specimen uptake and sample dispensing apparatus is shown in FIG. 2A where a modified dosing station 11' is depicted. In this arrangement, a flexbible conduit 28 connects the movable dosing tip assembly 21' to the dosing pump mechanism 30'. The movable dosing tip 24 is actuated by the process controller 33 to move through one of the openings in the guide 19 shown in FIG. 3. Movable tip 24 is shown in FIG. 2A as being inserted into a specimen tube 17 in a specimen tray 15 for aspirating specimen material. The dosing tip 24 may be withdrawn from the specimen receptacle 17 and may be moved by the tip transport means 21' transverse to the direction of tray advancement to dispense material to a plurality of other receptacles, either in the sample tray 14 or in receptacles both in sample tray 14 and specimen tray 15. Because of the gated communication through the valve 29', either specimen material alone or specimen material diluted by buffer material from the buffer reservoir 32 may be dispensed into the various receptacles in the trays 15 and 14. The movable dosing tip of assembly 21' is comprised of a backplate 22 and a tip support 23 rotatable together through conventional gearing about an axis 67 which extends through the support plate 154 secured a spaced distance from a vertical panel 18. At the lower portion of support plate 154 the guide 19 is positioned beneath the movable tip 24 and held in place by brackets 20. Guide 19 has a narrow ridge 55 extending in an arc about the axis 67. The lower end of the tip support 23 has a tip transport guide 54 with an inverted U-shaped cavity therein to accommodate the ridge 55. As the backplate 22 and tip support 23 rotate about the axis 67, they are guided in reciprocating motion by the ridge 55 and the tip transport guide 54.

Figure 3:
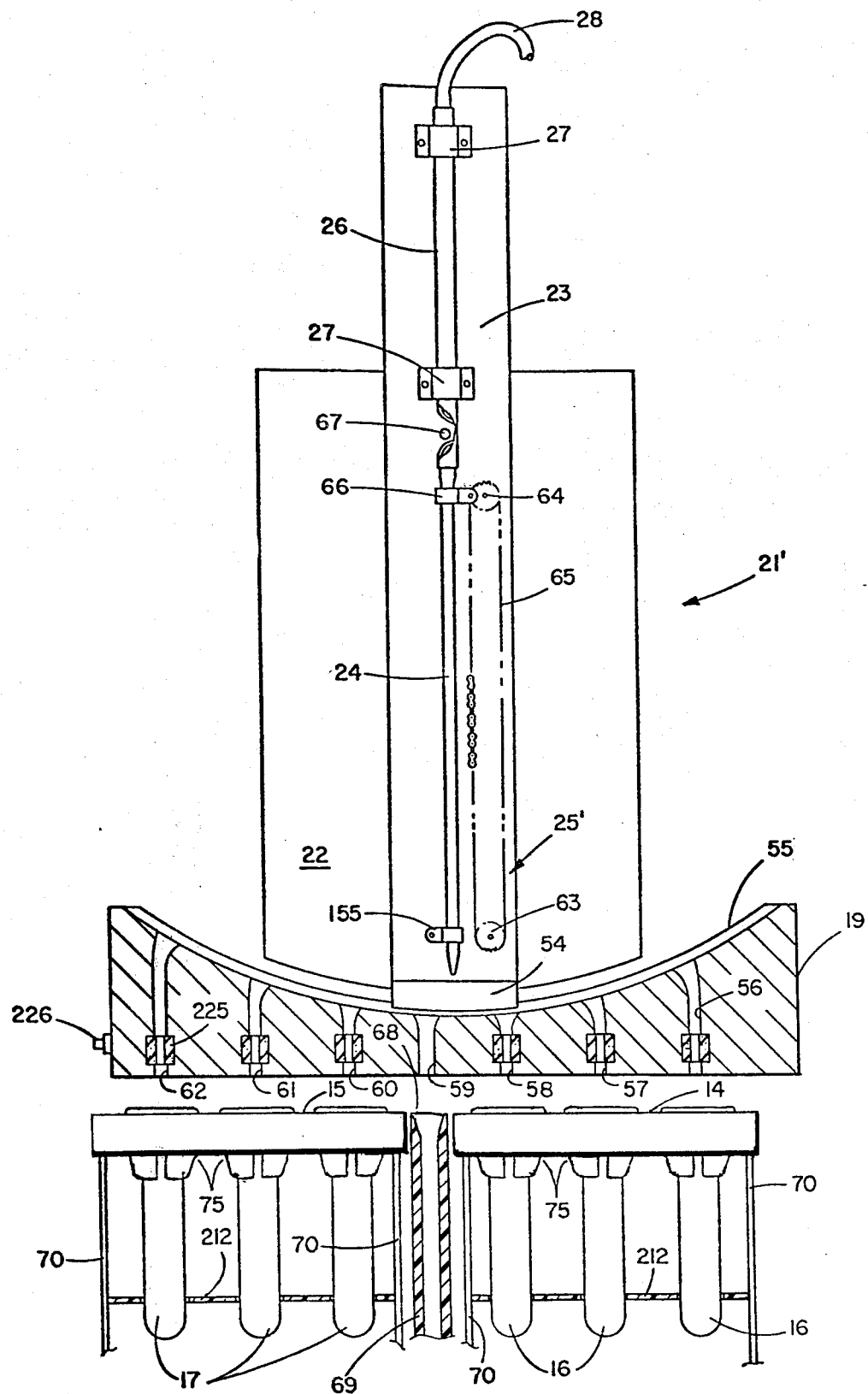
FIG. 3 is an enlarged view of the dosing means of FIG. 2A.

With particular reference to FIG. 3, the movable dosing tip assembly 21' at the start of a dosing cycle moves in a clockwise direction about the axis 67 so that the tip 24 is positioned in radial alignment with the upper extremity of the tip passageway 62. The process controller actuates the chain drive 25' through a motor (not shown) positioned on the reverse side of backplate 22 so that chain 65 advances in a counter-clockwise direction about the sprockets 63 and 64. Link 66, which is fastened both to the tip 24 and the chain 65, carries the tip 24 radially away from the axis 67 and into the tip passageway 62. The tip 24 is flexible, and the tip passageway 62 is shaped to deflect the tip 24 from its radial path and direct it down through the lower extremity of the tip passageway 62 and into the extreme left-hand specimen tube 17, as depicted in FIG. 2A. The process controller causes the specimen dosing pump to aspirate specimen material from this specimen tube 17. When aspiration is complete, the process controller causes the chain 65 to reverse direction and proceed in a clockwise manner about the sprockets 63 and 64. This draws the movable tip 24 back up through the tip guide passageway 62 so that the end of the tip 24 projects only slightly beyond the guide bracket 155 which is fastened to the guide 23. Similarly, the scouring section 26 is drawn back to a position where it is restrained by guide brackets 27. As tip 24 passes back up through passageway 62, a foam rubber sponge 225 inserted in a cavity in passageway 62 wipes off any liquid on the outside of tip 24 so as to preserve the integrity of the measured amounts to be dispensed. A vacuum line 226 connected to all of the sponges 225 in all of the passageways (except passageway 59) keeps the sponges in an unsaturated condition. This illustrated tip wiping arrangement is only one of several alternative means which can be employed for the desired purpose.

Figure 4:
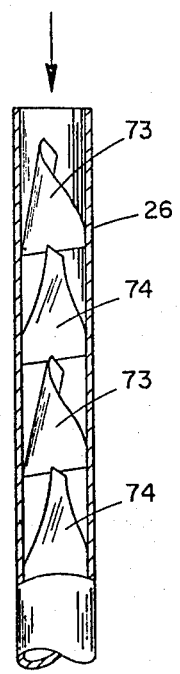
FIG. 4 is an elevational view in partial section of the scouring duct of FIG. 3.

The scouring section 26, as shown in FIGS. 2a, 2A and 3, appears in series with and immediately above the tips 24 of both embodiments and is a part of both the movable dosing tip assemblies 21 and 21'. The scouring section 26 is formed of a cylindrical duct, either rigid or flexible, as best illustrated in FIG. 4. Within the duct, a plurality of curved elements 73 and 74 extend longitudinally in a series. Each of the elements 73 and 74 extends to the interior of the duct walls throughout its length. The elements 73 and 74 may be a plastic, such as a polyolefin, plastic coated, stainless steel, glass, or formed of some other inert substance, and are arranged alternately and in point contact with each other. Cooperatively, these elements alternatively turn the direction of the flowing fluid proceeding in the direction indicated in FIG. 4. As can be seen, the edges of each element are transverse to the duct and are positioned at an angle to the contacting edges of the adjacent elements. That is, the upstream and downstream edges of the elements 74 are at an angle to the adjacent edges of the elements 73. Such a duct construction is illustrated in U.S. Pat. No. 3,286,992 which depicts a device for mixing fluids. To the contrary in this invention, however, the duct elements 73 and 74 are not used to mix fluids flowing simultaneously through the duct, but instead are used to separate fluids flowing sequentially through the duct. That is, while the general motion of the fluid through the scouring section 26 is in the direction of the arrow indicated in FIG. 4 when samples are being dispensed, there is also a scouring action imparted to the fluid by the elements 73 and 74. This scouring action effectively removes particles of specimen material or specimen and diluent materials which would otherwise cling to the walls of the scouring section 26 and creates an approximate plug flow profile which effectively minimizes intermixing of dissimilar fluids flowing sequentially through the tube. Once the tip 24 has been withdrawn into the retracted position of FIG. 3, the tip guide 23 and the back support 22 are free to rotate about the axis 67 as governed by the process controller. For example, once specimen material has been aspirated through the tip 24 extending through the tip guide passageway 62, the process controller may direct the valve 29' to allow buffer material to pass to pump 30' from the reservoir 32. The movable dosing tip assembly 21' may then be advanced counter-clockwise initially to dispense sample material comprised of specimen material aspirated from one of the tubes 17 into one or more of the sample receptacles 16. Exactly which sample tubes 16 are to be dosed is governed by the process controller 33. If all three of the sample receptacles 16 of FIG. 3 are to be dosed, the movable tip assembly 21' is rotated counter-clockwise so that the tip 24 is radially aligned with the tip passageway 58. Chain assembly 25' is actuated with the chain 65 proceeding in a counter-clockwise direction, and tip 24 is moved down through the tip passageway 58 and is directed by the curvature thereof into the left hand sample receptacle 16, where the dosing pump 30' causes a portion of the sample material to be dispensed. The chain assembly 25' quickly reverses direction, withdrawing the tip 24. The dosing tip assembly 21' is advanced slightly further in a counter-clockwise direction so that tip 24 is aligned with tip passageway 57. Chain assembly 25' is again actuated with tip 24 being guided downward to the center sample receptacle 16, where additional sample material is dispensed. Chain assembly 25' is again reversed, tip 24 is withdrawn, and tip assembly 21' rotated still further in a counter-clockwise direction. Chain assembly 25' is again actuated causing the tip 24 to proceed down the tip passageway 56 and into the right hand sample tube 16, where a further deposit of sample material is made. These three dosing operations result in the production of replicate samples of undiluted specimen material. The dilution of specimen material is achieved by clockwise rotation in FIG. 3 of tip assembly 21' to the second column position of specimen tray 15 and the dosing pump 30' dispenses the remaining quantity of specimen material plus sufficient buffer to effect the desired dilution. While still in this position the dosing pump 30' aspirates sufficient first dilution material to allow repetition of the dosing steps described above. Thereafter, the second dilution material is created, aspirated, and dispensed as described. After the deposit of the final sample necessary for the particular mixture of specimen and buffer material involved, as determined by process controller 33, the tip assembly 21' is moved in a clockwise direction and tip 24 is extended through tip guide 59 so that the remaining portion of that specimen-buffer mixture is emptied into a waste channel 68 in the sample preparation unit 10. A new cycle of aspiration and dispensation is then begun with a different specimen.

Immediately to the rear of the guide 19 in FIG. 2A is located a reagent addition means for adding reagent material from reagent reservoir means to receptacles in the sample trays 14. The reagent addition means of FIG. 2A is comprised of reagent dispensing tips 38, 39 and 40. These reagent dispensing tips are located at what may be termed reagent dosing positions above the sample tubes which are directly behind the sample tubes 16 illustrated in FIG. 3 at the sample dosing positions. While in many instances it may be desirable to dispense a single reagent into all of the samples 16, in other applications it may be desired to add different reagents to the sample tubes 16 in the different columns of the sample trays 14, in order to later check the replicate samples for separate reactions. This arrangement is illustrated in FIG. 2A wherein the reagent addition means, in addition to the three reagent dispensing tips, also includes the separate reagent reservoirs 51, 52, and 53, the peristaltic pump 47, and the valves 37. It should be noted that a dosing pump might be used in each fluid channel system in place of the peristaltic pump 47. It can be seen that reagent from the reagent reservoir 51 is conducted by conduit 48 through the peristaltic pump 47 or other pump means to the valve 37 associated with reagent dispensing tip 38. A recirculation connection conduit 43 extends from the valve 37 back to reservoir 51. This recirculation connection conduit 43 allows the peristaltic pump 47 or other pump means to continually circulate the reagent fluid through the system, so as to avoid variations in concentration of the reagent due to settling in the reservoir. Similarly, reservoir 52 is connected by conduit 49 through the pump means to the valve 37 associated with reagent dispensing tip 39. The recirculation line 42 allows reagent fluid to return to the reservoir 52. Reagent reservoir 53 is connected by line 50 through the pump means to the valve 37 associated with tip 40, and back to the reagent reservoir 53 by means of line 41. Each of the valves 37 is operated by the process controller through electrical leads 36, so that the appropriate amount or volume of each reagent from the reservoirs 51, 52, and 53 may be added to the different sample receptacle columns in the trays 14 respectively associated therewith. It can be seen that while samples are being prepared and dispensed through the movable tip assembly 21' at sample dosing positions in the dosing station 11', reagents are added to the sample receptacles which have just left the sample dosing positions and which are then advanced to the reagent dosing positions.

It can be seen that the process controller 33 of this invention is the basic unit governing operation of the sample preparation unit 10. FIG. 10 illustrates the process controller 33 in block form. Process controller 33 receives input instructions from the controls on the control panel indicated by the block labeled 72. In response, the process controller produces output instructions or control signals to the dilution control valve 29, the dosing pump 30, tip carriage or control 25, the reagent pumping means R, and the reagent valving V to govern fluid flow in the sample preparation unit. The reagent pumping means R includes the pumps 216i, 217, and 218i. Reagent valving V includes the reagent flow control valves and valve members 216, 216a, 216b, 216e, 216f, 216g, 216h, 217, 217a, 217b, 217e, 217f, 217g, 217h, 218, 218a, 218b, 218e, 218f, 218g, and 218h. In addition, the process controller provides instructions in the form of a control signal to the tray conveyor system 80 to govern tray advancement, including specimen and sample row advancement. An input from the code reading means 210 to the hardware interface circuit 300 is provided to correlate sample preparation data with specimen and sample identification, and a printed confirmation of specimen and sample treatment is provided at the print-out device P. The process controller chip 213 is connected to the hardware interface circuit 300, and has various storage and memory units connected to it. Among these units are the identification memory 301, read/write storage 302, micro-control bit memory 303, macro-control bit memory 304, temporary identification information storage 305, and timing memory 306.

The process controller 33 by providing the appropriate control signal governs the movement both of the sample trays 14 and the specimen trays 15 as well as the fluid flow between the specimen receptacles 17 and the sample receptacles 16. The process controller 33 also by providing an appropriate control signal governs fluid flow in the reagent addition means which may be used to introduce different reagents to each sample receptacle 16 in a row of sample receptacles which are located at the reagent dosing positions. The process controller carries out all of its required tasks according to predetermined instructions which are either programmed into the process controller 33 and stored in one of the memory units or which are manually entered into the process controller 33 through the instruction selection buttons labelled collectively as 72 in FIG. 10. In addition to the fluid and electronic circuits previously described, the process controller 33 utilizes a replication control circuit forming a part of either macro-control bit memory 304 or micro-control bit memory 303 and includes electronics providing a control signal for controlling the dosing means to distribute a plurality of predetermined replications of each specimen dilution into a plurality of sample receptacles 16. In this way, both dilutions and replications thereof of specimen materials may be produced during a single processing cycle of any particular specimen tray 15 and the associated sample trays 14. The sample receptacles associated with a particular specimen are located in the immediate physical vicinity of each other within the sample trays 14.

The process controller 33 is constructed to prepare batch controls and standards each time the unit operator indicates through controls 72 that a new processing cycle should be initiated. The batch controls are typically the first items prepared in the sample preparation unit 10 and typically include a sample for establishing total tracer activity (TC). This is a quantity of buffer material to which is added the standard aliquot of labelled material, but to which neither specimen material nor separation reagent is added. Also included in the batch controls is a wash blank referred to as the non-specific binding (NSB) sample to determine the experimental background. This sample is comprised of a quantity of buffer material to which the aliquot of labelled material has been added along with a separation reagent. Again, no active specimen material is added to this (NSB) sample. This control is used to determine the amount of radioactivity which binds to the sample tube 16 or separation reagent even though no active specimen material is present. Diluent is also typically present in the (NSB) sample. The third batch control that is usually used is a maximum binding sample ($B_0$). This maximum binding sample utilizes only half of the amount of buffer material which is used to make the (TC) and (NSB) samples, since binding reagent material is used to make up the equivalent volume. The ($B_0$) sample includes buffer, binding reagent material, separation reagent material, labelled tracer, and usually additional diluent. This batch control is used to determine the maximum radioactivity level which will result when only tracer labelled binding occurs.

After the batch controls, the process controller creates sample standards. These sample standards contain known amounts of the specimen material of interest in decreasing concentrations. These sample standards form reference points with respect to which unknown samples may be placed. After the sample standards are produced, unknown samples are typically prepared. Interspersed with or following these unknown samples are quality control samples. These quality control samples comprise known quantities of the specimen material of interest, and are similar in many respects to the sample standards. These quality control samples may be used as check points to determine the integrity of sample preparation or sample measurement.

The batch controls and sample standards are first prepared in the unit 10 before preparing any of the unknown samples. In the processing of the unknown samples, specimen materials and dilutions of specimen materials are prepared at the dosing station to produce unknown samples. Typically, a reagent is then added to the unknown samples at the reagent dosing positions. A possible step follows, followed by the addition of tracer labelled reagent. Again, incubation is usually followed by the addition of a separation reagent. Another incubation step may be desirable, after which the unknown samples with the added separation reagent are diluted. With the exception of the incubation steps, all of the foregoing processes are performed automatically in the apparatus of this invention. At the completion of sample preparation, the samples are ready for either filtration or centrifugation, which typically is followed by a count of radioactivity from the tracer labelled reagent.

Figure 8:
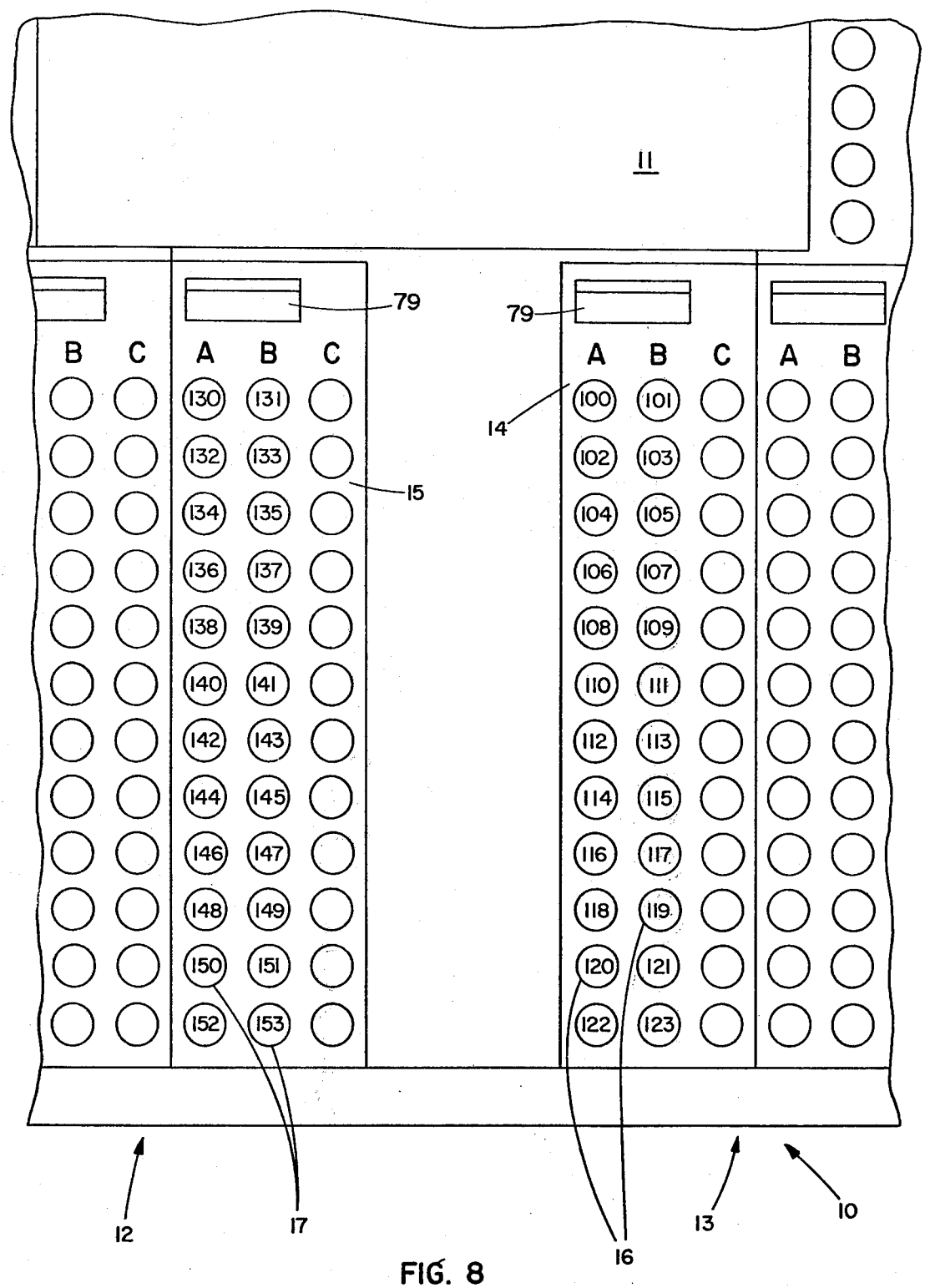
FIG. 8 is an isolated plan view of a specimen tray and a sample tray for positioning at the dosing station.

A typical control sequence of the process controller 33 may be illustrated by reference to FIG. 8, which depicts a speciment tray 15 having a rectangular array of receptacles in three columns and twelve rows. A sample tray 14 also contains three columns of twelve rows each of sample tubes 16. Both of the sample trays depicted in FIG. 8 have sample identification devices identical to those previously described. When the trays 15 and 14 are moved to the operating position beneath the dosing station 11 within their respective sections 12 and 13, the identification card is read and its contents transmitted to the process controller 33. The sample tray 14 and the specimen tray 15 are then advanced forward from the position depicted in FIG. 8 so that the specimen receptacles 130 and 131 and the sample receptacles 100 and 101 are in the sample dosing position.

A system will now be described whereby batch controls and standard samples are created, and duplicate samples of specimens and single dilutions thereof (dilution factor of 5, in this case), are created. The volumes of fluid mentioned in this discussion will be for purposes of example only, as the exact volume will depend on the competitive binding protocol utilized. However, as will be seen, the volumes of the different dilution concentrations placed in the sample trays is maintained at the same standard volume, as are the volumes of reagents added, through the computing facilities of process controller 33. Controller 33 takes into account the number of dilutions and replications, and reagents to be added to make up the samples, and maintains overall volume standards automatically, to insure compatibility and comparability between samples and successive trays. The sample tubes of tray 14 are all initially empty. The receptacle position 130 in specimen tray 15 contains a sample standard containing a known amount of specimen material of interest. If eight different concentrations of the standard are desired, the receptacles in positions 131 through 137 are empty. Unknown specimens then occupy the remaining evennumbered receptacles in the left hand column A of tray 15 with empty tubes occupying the odd-numbered receptacles of the center column B. Additional unknown specimens occupy the receptacles in the A column of succeeding trays. Because the replicates are to be made in duplicate in this example, test tubes are not needed in the right hand (C) column of receptacles in trays 14 and 15. Alternately, trays having only 2 columns could be used.

No aspiration steps are necessary to prepare the batch controls. Both trays are advanced under the dosing station 11, so that receptacles 130 and 131 of specimen tray 15, and receptacles 100 and 101 of sample tray 14, are at the dosing position initially. The TC samples are created by dispensing 200 microliters of buffer from reservoir 32 into tray positions 100 and 101 in tray 14. Tray 14 is then advanced one row and 200 microliters of buffer are added to positions 102 and 103 for creation of the NSB samples. Tray 14 is then advanced another row, and 100 microliters of buffer are added to each of the positions 104 and 105 for creation of the $B_0$ samples. Tray 14 is again advanced one row. 650 Microliters of the sample standard is aspirated from receptacle 130 of tray 15. 100 Microliters of this standard specimen are deposited in sample tray receptacles 106 and 107 having 450 microliters of standard specimen in the dosing means 450 Microliters of buffer is also drawn into pump 30, and then the remaining 450 microliters of sample standard specimen orginally aspirated followed by the 450 microliters of buffer are dispensed into specimen receptacle 131 forming the first dilution of the standard. Concurrently, the reagent dosing system dispenses 100 microliters of binding reagent into both receptacles 104 and 105. (Note that binding reagent is not added to receptacles 100, 101, 102, and 103.) Tray 14 is again advanced one row. 650 Microliters of fluid are aspirated from receptacle 131 and tray 15 is advanced one row while 100 microliters of the fluid from specimen receptacle 131 are dispensed to each of the sample receptacles 108 and 109. 450 Additional microliters of buffer are drawn into pump 30, and 450 microliters of diluted specimen material followed by 450 microliters of buffer are dispensed into specimen receptacle 132 to form a second dilution. Concurrently, 100 microliters of binding reagent are dispensed to receptacles 106 and 107 at the reagent addition position. Further dilution of the standard specimen material and replication of the sample standards is continued until receptacles 120 and 121 have been filled in the sample tray 15. At the completion of preparation of the batch controls and sample standards, the following conditions exist: Tray 15 is positioned under dosing station 11 with the fifth row of receptacles, positions 138 and 139, at the dosing position, and with decreasing concentrations of the specimen standard occupying tubes 130 through 137. Tray 14 is positioned under dosing station 11 with the twelfth row of receptacles, positions 122 and 123, at the dosing position, with TC samples occupying positions 100 and 101, with NSB samples occupying positions 102 and 103, with $B_0$ samples occupying positions 104 and 105, and with binding reagent having been added to receptacles 104 through 119, but not yet to receptacles 120 and 121.

After the diluted standard specimen occupying specimen tube 137 has been replicated into sample tubes 120 and 121, the excess specimen and buffer is disposed of through the waste channel 68. Now the system is ready to begin the preparation of samples from the unknown specimens. The procedure In each instance of specimen processing, 650 microliters of undiluted specimen material, commonly termed "neat" is aspirated from the specimen receptacle in column A of the specimen tray at the dosing position and 100 microliters dispensed as duplicate specimens into each of the receptacles of columns A and B of the sample tray row which is then located at the dosing position. Concurrently with this replication of the specimen, the reagent addition means 11B is dosing a preceding row of sample receptacles with binding reagents. 1800 Microliters of buffer is drawn into pump 30, 450 microliters of specimen material previously aspirated is then dispensed into the adjacent specimen receptacle in Column B of the same row, followed by the 1800 microliters of buffer. The sample tray is advanced one row to bring a succeeding sample row to the dosing position. 650 microliters of diluted specimen are thereafter aspirated from the receptacle in column B of the specimen tray 15 at the sample dosing station. This solution is then replicated into the receptacles in the succeeding row of the sample tray 14 as the receptacles of the immediately preceeding sample are being dosed with binding reagent. Subsequent unknown specimens are processed in the same manner, usually with a replication of the specimen into a row of the sample tray receptacles, followed by the making of a dilution and its replication into the next row of the sample ray, while the appropriate reagent is added to the preceding sample row.

When row 12 of tray 14 has been processed, the reagent dosing means adds binding reagent to the receptacles of the twelfth row and the tray conveyor means 80 beneath sample section 13 moves all sample trays clockwise (FIG. 1) until the first row of the next sample tray is positioned at the dosing position. Before the next sample tray is moved into position, its identification card is interrogated for sample identification by the readout unit 204. The excess specimen and buffer is disposed of through the waste channel 68. Processing of specimens continues until all specimens have been replicated and all samples have been dosed with binding reagent.

After incubation (if required), all samples will be recycled through sample 13 for the addition of a uniform quantity of tracer labelled reagent to all sample receptacles. After further incubation, again only if required, all samples with the exception of the total count (TC) samples will be recycled through the sample section 13 for the addition of a separation reagent. This completes the operations performed by the preparation unit on the samples. If incubation is not required between the addition of the various reagents, more than one reagent may be added to each receptacle on a particular pass through the machine, thus reducing the number of times the samples must be cycled through the machine. Up to three different reagents may be dispensed into each sample receptacle on a single pass through the sample preparation unit 10 using the reagent addition means of FIG. 2. It can be seen that, depending upon the chemical substances involved, it may be possible to completely prepare the samples on a single pass of the sample receptacles through the unit 10. In all instances, however, the sample dilutions and replications are established on a single pass through the unit 10 and subsequent processing in the unit 10 is only for adding uniform amounts of material to the sample receptacles.

The sequence of operations in the stages of sample dosing in the example described are pertinent only for the particular number of dilutions and replications described. Numerous modifications in these steps are appropriate where there are any deviations from the example used. Furthermore, there is a wide variance in the reagent dispensing steps which follow the sample dosing steps that are carried out in the apparatus of this invention. Accordingly, the foregoing descriptions, illustrations, and examples should be considered as merely explaining the essence of this invention, as numerous modifications and variations will be obvious to those skilled in the field of competitive binding assay.

We claim:

1. A method for preparing samples, including dilutions of a specimen and replication of said specimen and dilution thereof, for use with a source of diluent, and sample preparation apparatus including a dosing tip, a dosing pump means in gated communication with said tip and said diluent source, and a process controller for providing command signals coordinating and governing operation of said apparatus, said method comprising the steps of:

aspirating a specimen of a given dilution thereof into said dosing tip by means of said pump, in response to first command signals from said process controller;

dispensing in proportional fractions a portion of said specimen or given dilution by means of said dosing pump means in response to second command signals through said dosing tip into a plurality of replication receptacles to replicate said specimen or given dilution;

aspirating a quantity of diluent from said diluent source into said pump means in response to third command signals, dispensing the remaining specimen or given dilution previously aspirated, along with said quantity of diluent, by means of said dosing pump means in response to fourth command signals through said dosing tip into a holding receptacle to form a subsequent dilution.

2. A method as in claim 1, in which said steps are repeated for said subsequent dilution, and again for as many times as necessary to form a plurality of further subsequent dilutions.

3. A method as in claim 1, in which said sample preparation apparatus also includes a means for inhibiting intermixing between different fluids flowing through said tip, and said pump means in performing said steps of aspirating and dispensing of specimen, dilution thereof and diluent drives said fluids through said means for inhibiting intermixing.

4. A method as in claim 1 in which in said step of aspirating a specimen or given dilution, and in said step of dispensing replicates, the volume aspirated and the total portion of the volume dispensed for replicates may be varied under the control of said process controller.

5. A method as in claim 1 in which said aspirating of diluent by said pump is made directly from said diluent source.

6. A method as in claim 1 in which said dispensing steps are performed by sequentially dispensing first the specimen or given dilution, and secondly, the diluent.

7. A method as in claim 1, in which said sample preparation apparatus also includes a plurality of reagent source means, reagent outlet means positioned to cooperate with said repliction receptacles, and valved reagent pump means connecting said reagent source means with said ouelet means and responding to fifth command signals and in which said method further includes the step of dispensing from said outlet means into said dilutions and replicates thereof by said valved pump means in response to fifth command signals a controlled variable volume of one or more reagents of said plurality of reagent sources preselected for each such dilution and replicate.

8. A method as in claim 1, in which, in said step of aspirating diluent, said quantity aspirated is variable by said pump means and said process controller.

9. A method as in claim 8 in which the dilution ratio between said given dilution and said subsequent dilution is variable, and said diluent quantity is aspirated in accordance with the selected dilution ratio and the quantity of said specimen or given dilution remaining in said tip after said replications are dispensed.

10. A sample preparation apparatus for use with trays having a plurality of receptacles, for diluting and replicating chemical specimens to automatically establish samples and sample standards for subsequent analysis, said apparatus including means for supplying buffer and a plurality of means for supplying reagents, said apparatus comprising:
 means for advancing said trays, said means conveying ones of said trays containing discrete specimens, and others of said trays for containing discrete samples in respective separate paths in response to first control signals;
 buffer and specimen processing means positioned at a dosing position adjacent both said paths, said processing means being responsive to second control signals and in gated communication with said buffer supplying means to intake variable volumes of buffer, and specimen or dilutions thereof, for producing a predetermined number of different dilutions of said specimen from single ones of said specimen receptacles, and for dispensing said specimen, said different dilutions thereof and replicates thereof, as required
 reagent addition means having outlet means positioned at a predetermined reagent addition position adjacent said path of said sample trays downstream of said dosing position, said reagent addition means being responsive to third control signals and in gated communication with one or more of said plurality of reagent supplying means to dispense through said outlet a selected one or more of said different reagents to individual ones of the sample tray receptacles as said ones of said receptacles pass said reagent addition position;
 and process control means supplying said control signals for governing said tray advancing means, said dosing means and said reagent addition means to determine the number of dilutions and replicates thereof and the reagents for each sample and replicates thereof, to produce automatically the dilutions, replicates and standards needed for subsequent analytical processing.

11. A sample preparation apparatus as in claim 10, in which said process control means includes computer means to calculate and adjust automatically the volume to be aspirated and dispensed in view of the number of dilutions, replicates and reagents selected, to insure the comparability of the samples.

12. A sample preparation as in claim 10, in which said processing means includes first valve means providing said gated communication between said buffer supplying means and processing means, and first pump means also connected to said first valve means, said first pump means also being gated by said first valve means and responding to said second control signals and moving variable volumes to aspirate material from single ones of said specimen receptacles, effect the uptake of buffer, and discharge specimen and buffer to produce said dilutions, as well as dispensing said replicates and dilutions.

13. A sample preparation appartus as in claim 12, in which said first valve means has a first operating position in which said specimen processing means replicates, and a second operating position in which said specimen processing means dilutes, said operating position being selected by said process controller, said first pump means aspirating specimen and dispensing to one or more sample tray receptacles to create one or more specimen replicates with said first valve means in said first position, said first valve means in said second position communicating with said buffer means with said first pump means drawing in buffer, and depositing it, along with previously aspirated specimen in one of said unoccupied specimen tray receptacles to create a first dilution, said first valve means then returning to said first position while said first pump means aspirates from said one unoccupied receptacle and dispenses said first dilution, either into a single sample receptacle, or to a plurality thereof, to furnish replicates of said dilution.

14. Sample preparation apparatus as in claim 13 in which said tray receptacles are arranged in a rectangular array of a multiplicity of rows and at least two columns, said tray advancing means conveying both said specimen trays and said sample trays in the direction of said columns, and in which said specimen processing means further includes a single movable dosing tip connected to said first pump means, and tip transport meas activated by said process controller for moving said dosing tip transverse to the direction of tray advancement at said dosing position with the movement of said tip transport means being aligned in the direction of said rows and moving said tip between a first receptacle of a first one of said rows on a specimen tray and a sample tray during said first valve operating position and said replication of said sample, said tip transport means moving said tip to an auxiliary receptacle of said first specimen tray row during said second valve operating position and said creation of said first dilution, said tray advancing means then moving said sample tray to being a subsequent row into the dosing position, said valve means returning to said first position and said tip transport means moving said tip between said auxiliary receptacle and a first sample receptacle of a subsequent row of said sample tray, with replicates of said first dilution being dispensed into adjacent receptacles of said subsequent row.

15. A sample preparation apparatus as in claim 12, in which said buffer and specimen processing means further includes a single movable dosing tip connected to said first pump means, and serving as the sole outlet for said buffer supplying means to said tray receptacles, as well as the sole intake for aspirating specimen and the sole outlet for discharging said replicates and dilutions.

16. A sample preparation apparatus as in claim 15 in which said processing means further includes tip transport means activated by said process controller for moving said dosing tip transverse to the direction of tray advancement at said dosing portion from a first specimen receptacle to one or more sample tray receptacles for said aspirating and dispensing of said specimen replicates, and then to one of said unoccupied specimen tray receptacles for said dilution production, and again to one or more of said different sample tray receptacles for said dispensing of said dilutions and replicates thereof.

17. A sample preparation apparatus as in claim 10, in which said reagent addition means also comprises valve means connected to two or more of said reagent supplying means to provide said gated communication between said reagent addition means and said reagent supplying means, said reagent outlet means being positioned above said reagent addition position and connected to said valve means, said reagent addition means further comprising pump means connected to said valve means to more variable volumes of reagent and dispense in accordance with said third control signals any selected one of said different reagents through said outlet means into individual sample receptacles at said reagent addition position.

18. A sample preparation apparatus as in claim 17 in which said reagent addition means further includes a plurality of said valve means, and a like plurality of said pump means and a salt outlet means each respectively connected with one of said valve means, each of said valve means connected to a respective plurality of reagent supplying means, said outlet means plurality being physically closely adjacent to enable all to dispense into individual ones of said sample receptacles at said reagent addition station any selected one of said different reagents, or a plurality of said different reagents simultaneously, in response to said third control signals.

19. A sample preparation apparatus as in claim 18, in which said tray receptacles are arranged in a rectangular array of a multiplicity of rows and at least two columns, said tray advancing means conveying said sample tray in the direction of said columns past said reagent addition position, and in which said plurality of outlet means is duplicated for each of said tray columns and positioned above each adjacent receptacle of a sample tray row at said reagent addition position, to enable all of the sample receptacles of said row to receive the selected one or more reagents.

20. A sample apparatus as in claim 19, in which each of said plurality of valve means is in gated communication with a respective one of each outlet means plurality associated with a tray column, so that each valve means in response to said third signals from said process controller either may communicate alternatively with any of said outlet means, or may communicate with all of said outlet means simultaneously, whereby each sample receptacle of a sample tray row at the reagent addition position receives a different reagent, or receives simultaneously the same combination of reagents.

21. A sample preparation apparatus as in claim 17 in which said valve means comprises a reagent reservoir switching valve, a pump control valve, and a dispensing valve, all in series in a closed fluid circuit, with said pump control valve also being connected to said pump means, and said dispensing valve being connected to said outlet means, all of said valves responding to said third control signals, said reagent switching valve selecting one reagent reservoir for supplying said closed circuit, said pump control valve connecting said pump means in an uptake mode to said circuit to draw off said selected reagent, and thereafter switching to a circulating position with said pump means in a discharge mode to circulate said reagent through said circuit, said dispensing pump opening said closed circuit into said outlet means to said circuit with said pump in a discharge mode and said control valve in said circulating position to dispense the selected reagent.

22. A sample preparation apparatus as in claim 21, in which said tray receptacles are arranged in a rectangular array of a multiplicity of rows and at least two columns, said tray advancing means conveying said sample trays in the direction of said columns past said reagent addition position, and in which said circuit also includes additional dispensing valves, and additional outlet means each outlet means being connected to a respective one of said dispensing valves, each of said dispensing valves being connected in series in said closed fluid circuit, each outlet means being spaced from the adjacent outlet means so as to be positioned above adjacent receptacles of a sample tray row at said reagent addition position, to enable all of the sample receptacles of said row to receive the selected reagent.

23. A sample preparation apparatus as in claim 21, in which said reagent addition means also includes a waste valve for each reagent reservoir between said reagent switching valve at each reagent reservoir, said waste valve opening prior to said reagent switching valve selecting another reagent and said pump means moving into discharge mode to purge said circuit.

24. A sample preparation apparatus as in claim 23 in which said single movable dosing tip constitutes the sole outlet of said buffer supplying means to said tray receptacles.

25. A sample preparation apparatus for diluting and replicating in one operating cycle, for use with means for supplying buffer and trays having a plurality of receptacles, said apparatus comprising:

tray advancing means for conveying at least one of said trays containing a plurality of discrete specimens, and others of said trays for containing discrete samples, said means independently conveying sample and specimen trays in respective separate but adjacent paths in response to first control signals;

sample dosing means positioned at a dosing position adjacent both said paths and including pump means in gated communication with said buffer supplying means, said sample dosing means responding for each of said specimens to second control signals for aspirating said specimen or a given dilution thereof and intaking buffer in controlled variable volumes for discharging same into an unoccupied specimen tray receptacle to produce a selected subsequent dilution, and for aspirating said subsequent dilution and dispensing a portion of such subsequent dilution into one or more sample tray receptacles to produce one or more replicates of said selected subsequent dilutions;

and a process controller supplying said first and second control signals for governing respectively said tray advancing means and said sample dosing means in coordination with each other, to provide selected dilutions and replicates automatically in one operating cycle.

26. A sample preparation apparatus as in claim 25, in which both said specimen tray path and said sample tray path is a closed loop, and said tray advancing means maintains said trays in a generally horizontal attitude throughout said closed loop paths.

27. A sample preparation apparatus as in claim 25, in which said sample dosing means includes a single movable dosing tip supported above said dosing position, and means for moving said tip between ones of said specimen receptacles, as well as between specimen receptacles and sample receptacles at said dosing position, said aspirating and dispensing being accomplished through said single tip.

28. A sample preparation apparatus as in claim 27, in which said dosing means further include means upsteam of said tip for imparting a plug flow profile and a scouring action to fluid passing through said means to dislodge clinging particles of specimen and to minimize intermixing of sequentially flowing fluid.

29. A sample preparation apparatus as in claim 28, in which said means for imparting plug flow and scouring motion includes a cylindrical duct, a plurality of curved elements in series longitudinally within said duct, each element extending throughout its length to the interior of the duct walls, said elements being arranged alternately and in point contact with each other and having curvature to turn the direction of the flowing fluid, the edges of each element transverse to the duct being positioned at an angle to the contacting edges of the adjacent elements, said elements imparting a scouring action during movement of fluid therethrough to remove particles of specimen as well as imparting an approximate plug flow profile to said fluid to minimize intermixing of sequentially flowing fluids.

30. Apparatus for preparing specimens into samples for subsequent analysis for use with trays having a plurality of receptacles retaining discrete specimens, as well as other like trays retaining said samples, said apparatus having tray advancing means for conveying said specimen trays and sample trays in separate but adjacent paths the improvement comprising:
    dilution and replication processing means positioned at a first dosing position common to both said paths, for intaking and dispensing controlled variable volumes of specimen, dilutent and samples to produce a selected one or more of a plurality of predetermined dilutions of said discrete specimens, as well as replicates of said specimens and of said dilutions thereof, and deposit said replicates in said sample trays; and
    means at a second dosing position adjacent said path of said sample trays for dispensing to individual ones of said sample tray receptacles controlled variable volumes of one or more different reagents preselected for the sample deposited in each such individual receptacle.

31. Apparatus as in claim 30, which further includes process control means supplying said control signals for governing said tray advancing means, said processing means, and said reagent addition means in coordination with each other to provide selected dilutions, replicates thereof, and of specimen, and selected additions of reagent thereto in one operating cycle.

32. Apparatus as in claim 30, in which said tray receptacles are arranged in a rectangular array of rows and columns, and said processing means includes means for dispensing each respective dilution and specimen replicate into a respective receptacle of a column of said sample tray, with respective replicates of a given specimen or dilution being dispensed into adjacent receptacles of one row.

33. Apparatus as in claim 32, in which said means for dispensing reagent cooperates with a plurality of reagent source means and includes outlet means for each of said tray columns positioned downstream of said first dosing position over said sample tray path, with said reagent dispensing means in gated communication with said plurality of reagent source means, to dispense a selected one or more reagents from said outlet means simultaneously to individual ones of said sample tray receptacles in the sample tray row at said second dosing position.

34. In a sample preparation apparatus for diluting and replicating for use with means for supplying diluent and trays having a plurality of receptacles, said appartus having tray advancing means for conveying said trays in response to first control signals, the improvement comprising:
    sample dosing means in gated communication with said diluent supplying means, said dosing means including a single pump and responding to second control signals and intaking variable volumes of a specimen or dilution thereof, and variable volumes of diluent, for both producing a selected one or more of a plurality of dilutions of said single specimen, as well as for producing one or more replicates of each of said specimens and of said selected dilutions;
    and a process controller supplying said first and second control signals for governing and coordinating the operation of said tray advancing means and said sample dosing means to provide selected dilutions and selected replications.

35. Apparatus for preparing samples for use with a source of diluent, to prepare dilutions of specimen, and replication of said specimen as well as of said dilutions, said specimen, dilutions and replications being contained in open receptacles held in a horizontal array, said apparatus comprising:
    a dosing tip for intaking and passing fluid from and into said receptacles;
    transport means for bringing said tip and receptacles into registration, with said tip over said receptacles, and for moving said tip between receptacles and into and out of said receptacles, in response to first control signals;
    pump means in gated communication with said diluent source and said dosing tip and having three operating states, for aspirating through said dosing tip variable volumes of specimen or dilutions thereof in a first operating state, for aspirating variable volumes of dluent in a second operating state, and for driving all or a proporational fraction of aspirated materials through said dosing tip in a third aspirating state, said pump means assuming one or another of said operating states in response to second control signals;
    and process control means supplying said first and second control signals and coordinating same for controlling and operating said transport means and pump means, said control means placing said pump means in said first and second operating states to produce a derived dilution, and in said first and third states to replicate said dilution, whereby selected dilutions of said specimen and selected replications of said dilutions or specimen are produced in one operating cycle.

36. Apparatus as in claim 35, in which in response to said control means and upon aspiration of a dilution or specimen, said transport means moves said tip serially over a predetermined plurality of receptacles during said third operating mode, and said pump dispenses an equal portion of said aspirated material to each receptacle of said predetermined plurality.

37. Apparatus as in claim 35, in which said pump means is comprised of a single group and a valve means providing said gated communiction between said tip and said diluent source, said valve means responding to said second control signals to connect said diluent source to said pump so as to dispense diluent sequentially after the dispensation of the specimen or previous dilution, when making a new dilution.

38. Apparatus as in claim 35, in which said pump means further includes a linear actuator responding to said second control signals to facilitate the dispensing of proportional fractions of previously aspirated materials and precise control over the variable volumes of diluent and specimen processed by said pump means.

39. Apparatus as in claim 35, which further includes a plurality of reagent source means, reagent outlet means positioned to cooperate with said receptacles, and a reagent source switching valve, a pump control valve, a dispensing valve, all in series in a closed fluid circuit, and a reagent pump cooperating with said pump control valve, said process control means providing third signals controlling and operating said valves and pump, whereby said reagent switching valve selects one of said reagent source means for supplying said closed circuit, said pump control valve connects said reagent pump in an uptake mode to said control circuit to draw off the reagent selected, and thereafter switches to a circulating state with said reagent pump in a discharge mode to circulate said reagent through said circuit, said dispensing pump being in gated communication with said outlet means and opening said circuit to said outlet means with said reagent pump in discharge mode and said pump control valve in a circulating state to dispense the selected reagent.

40. Apparatus as in claim 35, which further includes means connected in series with said tip between said tip and said pump means for inhibiting intermixing between different fluids sequentially flowing through said tip.

41. Apparatus as in claim 40, in which said means for inhibiting intermixing includes a hollow fluid conduit, at least one element aligned in the direction of the axis of conduit and rotatable generally about said axes, said element having a configuration to rotate and thereby to impose a plug flow pattern on fluids passing said element in response to the motion of said fluids such that intermixing between sequentially flowing dissimilar fluids is minimized.

42. Apparatus as in claim 41, in which said element has a configuration which imposes a scouring motion as well as said plug flow pattern on fluids passing said element.

43. Apparatus as in claim 41, in which said element includes one or more surfaces which are curved, and in which said means for inhibiting intermixing includes a plurality of said elements in series.

* * * * *